(12) United States Patent
Yates-Binder et al.

(10) Patent No.: US 11,338,017 B2
(45) Date of Patent: May 24, 2022

(54) SMALL PEPTIDE COMPOSITIONS AND USES THEREOF

(71) Applicants: University of Pittsburgh—Of the Commonwealth System of Higher Education, Pittsburgh, PA (US); Tuskegee University, Tuskegee, AL (US)

(72) Inventors: Cecelia C. Yates-Binder, Pittsburgh, PA (US); Jesse Jaynes, Tuskegee, AL (US)

(73) Assignees: University of Pittsburgh—Of the Commonwealth System of Higher Education, Pittsburgh, PA (US); Tuskegee University, Tuskegee, AL (US)

( * ) Notice: Subject to any disclaimer, the term of this patent is extended or adjusted under 35 U.S.C. 154(b) by 392 days.

(21) Appl. No.: 16/370,603

(22) Filed: Mar. 29, 2019

(65) Prior Publication Data

US 2019/0298802 A1    Oct. 3, 2019

Related U.S. Application Data

(60) Provisional application No. 62/662,987, filed on Apr. 26, 2018, provisional application No. 62/663,003, (Continued)

(51) Int. Cl.
*A61K 38/19* (2006.01)
*A61P 9/10* (2006.01)
(Continued)

(52) U.S. Cl.
CPC .............. *A61K 38/195* (2013.01); *A61P 9/10* (2018.01); *A61P 35/00* (2018.01); *C07K 7/02* (2013.01);
(Continued)

(58) Field of Classification Search
CPC .......... A61K 38/195; A61P 35/00; A61P 9/10; C07K 14/001; C07K 7/02; C07K 7/08; C12N 15/113; C12N 15/62; C12N 15/86
See application file for complete search history.

(56) References Cited

U.S. PATENT DOCUMENTS 8,734,775 B2    5/2014   Yates-Binder et al.
9,180,167 B2   11/2015   Wells et al.
(Continued)

OTHER PUBLICATIONS

Altara et al., "The CXCL10/CXCR3 Axis and Cardiac Inflammation: Implications for Immunotherapy to Treat Infectious and Non-infectious Diseases of the Heart," *J. Immunol. Res.*, 12 pp., 2016.
(Continued)

*Primary Examiner* — Randall L Beane
(74) *Attorney, Agent, or Firm* — Klarquist Sparkman, LLP

(57) ABSTRACT

Interferon-γ-inducible protein 10 (IP-10) peptides, IP-10 peptide variants and in silico designed C-X-C chemokine receptor 3 (CXCR3) peptide agonists are described. The small peptides can be used for inhibiting pathological tissue remodeling and treating fibrosis in a subject, such as a subject with fibrosis of the heart, lung, liver, kidney or skin. The peptide agonists can also be used to treat cardiovascular disease, including myocardial infarction and ischemia-reperfusion injury. Also described are in silico designed peptide antagonists that bind CXCR3 or ligands of CXCR3. These antagonist peptides block CXCR3 signaling by disrupting interaction of CXCR3 with its ligand. Antagonist peptides can be used, for example, to treat myocarditis and atherosclerosis. In additional embodiments agonists and antagonists of CXCR4 are disclosed.

18 Claims, 10 Drawing Sheets

Specification includes a Sequence Listing.

Related U.S. Application Data filed on Apr. 26, 2018, provisional application No. 62/650,719, filed on Mar. 30, 2018.

(51) Int. Cl.

| | | |
|---|---|---|
| *A61P 35/00* | (2006.01) | |
| *C12N 15/62* | (2006.01) | |
| *C12N 15/86* | (2006.01) | |
| *C07K 7/02* | (2006.01) | |
| *C12N 15/113* | (2010.01) | |

(52) U.S. Cl.
CPC ............ *C12N 15/113* (2013.01); *C12N 15/62* (2013.01); *C12N 15/86* (2013.01)

(56) References Cited

U.S. PATENT DOCUMENTS

| | | |
|---|---|---|
| 9,895,419 B2 | 2/2018 | Yates-Binder et al. |
| 2013/0053319 A1 | 2/2013 | Yates-Binder et al. |
| 2014/0178451 A1 | 6/2014 | Wells et al. |
| 2016/0022872 A1 | 1/2016 | Wells et al. |
| 2017/0000852 A1 | 1/2017 | Yates-Binder et al. |

OTHER PUBLICATIONS

Bodnar et al., "IP-10 Blocks Vascular Endothelial Growth Factor-Induced Endothelial Cell Motility and Tube Formation via Inhibition of Calpain," *Circ Res* 98:617-625, 2006.

Burdick et al., "CXCL11 Attenuates Bleomycin-Induced Pulmonary Fibrosis via Inhibition of Vascular Remodeling," *Am. J. Respir. Crit. Care Med.*, vol. 171:261-268, 2005.

Espinoza et al., "Inhibiting Cardiac Fibrosis in Myocardial Infarction by CXCL 10 Agonist Peptide," *FASEB J.*, vol. 30(1), Supplement 1178, Apr. 1, 2016.

Frangogiannis et al., "Chemokines in Myocardial Ischemia," *Trends Cardiovasc. Med.*, vol. 15:163-169, 2005.

Jiang et al., "Regulation of Pulmonary Fibrosis by Chemokine Receptor CXCR3," *J. Clin. Invest.*, vol. 114:291-299, 2004.

Ornelas et al., "Small Peptide Antagonists Derived Based on in Silico Analysis Block CXCL10-CXCR3 Signaling and Function on Cardiac Fibroblasts and Cardiomyocytes," *FASEB J* 2017 31:1_supplement, 984.1, Apr. 1, 2017.

Yates et al., "Matrix Control of Scarring," *Cell Mol. Life Sci.*, vol. 68:1871-1881, 2011.

Yates, et al., "Lack of CXC Chemokine Receptor 3 Signaling Leads to Hypertrophic and Hypercellular Scarring," *Am. J. Pathol.*, vol. 176:1743-1755, 2010.

Yates et al., "Skin Wound Healing and Scarring: Fetal Wounds and Regenerative Restitution," *Birth Defects Res. C. Embryo Today*, vol. 96:325-333, 2012.

Yates et al., Transplanted Fibroblasts Prevents Dysfunctional Repair in a Murine CXCR3-Deficient Scarring Model, *Cell Transplant.*, vol. 21:919-931, 2012.

Yates-Binder et al., "An IP-10 (CXCLIO)-Derived Peptide Inhibits Angiogenesis," *PLoS ONE*, vol. 7:e40812, 2012.

Yuan et al., "CXCL10 Inhibits Viral Replication Through Recruitment of Natural Killer Cells in Coxsackievirus B3-Induced Myocarditis," *Circ. Res.*, vol. 104:628-638, 2009.

Yue et al., "Direct Gene Transfer with IP-10 Mutant Ameliorates Mouse CVB3-Induced Myocarditis by Blunting Th1 Immune Responses," *PLoS ONE*, vol. 6:e18186, 2011.

SMALL PEPTIDE COMPOSITIONS AND USES THEREOF

CROSS REFERENCE TO RELATED APPLICATIONS

This application claims the benefit of priority to U.S. Provisional Application No. 62/650,719, filed Mar. 30, 2018, U.S. Provisional Application No. 62/662,987, filed Apr. 26, 2018 and U.S. Provisional Application No. 62/663,003, filed Apr. 26, 2018. The above-listed applications are herein incorporated by reference in their entirety.

ACKNOWLEDGMENT OF GOVERNMENT SUPPORT

This invention was made with government support under grant number AR068317 awarded by the National Institutes of Health. The government has certain rights in the invention.

FIELD

The present disclosure concerns IP-10 peptides and in silico designed peptide agonists and antagonists the CXCR3 signaling pathway, as well as use of the peptides, such as for treating fibrosis, myocarditis and cardiovascular diseases.

BACKGROUND

Heart failure (HF) currently accounts for one in every eight deaths in the United States. Due to increasing frequency of comorbidities such as obesity, the prevalence of this disease is expected to increase 46% by 2030. After a coronary event such as myocardial infarction (MI), unregulated fibrosis in the infarct region leads to stiffening of the ventricle wall. Over time, the scar continues to expand throughout the ventricle wall, leaving it too stiff and weak to contract efficiently until HF occurs. Evidence suggests that initial scar formation is necessary to prevent ventricle rupture immediately after MI, but long-term upregulation of fibrotic transforming growth factor beta 1 (TGFβ1), matrix metalloproteinases (MMPs), and myofibroblast activation lead to adverse ventricular remodeling and ultimately heart failure. Morbidity and mortality arising from HF has been linked directly to the extent of fibrosis within the ventricle. This suggests that inhibition of fibrosis after MI will reduce the incidence of heart failure.

Fibroblasts are abundant within the healthy adult myocardium and serve as sentinel cells to detect damage and trigger the repair of tissue. Their abundance allows them to infiltrate quickly and create a collagen matrix, maintaining mechanical integrity of the ventricle in the acute phase of MI. Infiltrating inflammatory cells such as neutrophils secrete TGFβ1 and inflammatory cytokines, leading to activation of fibroblasts. These activated myofibroblasts upregulate α-smooth muscle actin (aSMA) transcription, activate SMAD-dependent signaling, and increase expression of non-fibrillar collagen. Prevention of myofibroblast activation and its downstream effects reduces late-stage fibrosis and remodeling leading to HF.

According to the World Health Organization (WHO), ischemic heart disease is the most common cause of death in the world. In the United States, an estimated 785,000 individuals per year will have a myocardial infarction (MI) which equates to approximately 1 event per minute. Adverse remodeling that occurs post-MI contributes to the impaired function and heart failure that is associated with increased morbidity and mortality. Advances made in interventional therapies, largely early reperfusion therapies, have improved patient survival, while increasing morbidity and mortality of the resulting heart failure. The size of the infarcted area, infarcted wound healing and chronic left ventricular remodeling are the factors that determine the extent of heart failure. Therapeutic strategies are needed to limit infarct wound healing in the early phase of disease in order to minimize the severity of heart failure, particularly after a large or recurrent MI.

Myocarditis is an inflammatory disease of the heart muscle that can manifest as heart failure and cardiogenic shock, or result in life-threatening rhythm disturbances. There is a diverse group of factors that cause myocarditis, including viral, bacterial and parasitic infections, as well as autoimmune disorders. The severe cardiac inflammation that characterized myocarditis is mediated by leukocytes entering the cardiac tissue, and is often accompanied by remodeling and cardiomyocyte apoptosis. Current therapeutic options rely heavily upon clinical management of symptoms and not the underlying pathogenesis.

Atherosclerosis is a disease in which plaque accumulates in the arteries and hardens, leading to a narrowing of the arteries. Atherosclerosis can lead to circulatory problems, heart attack, heart failure, stroke and death. Treatment for atherosclerosis generally includes lifestyle changes, such as improved diet, weight loss, stress management and exercise, in addition to medications that lower cholesterol or blood pressure. For patients with severe atherosclerosis, surgical procedures are often advised, including angioplasty or coronary artery bypass. Inflammation is known to play an important role in the development and pathogenesis of atherosclerosis (Spagnoli et al., *J Nucl Med* 48(11):1800-1815, 2007; Wu et al., *Int J Mol Sci* 18:2034, 2017), thus a need exists for immune related therapeutic interventions.

SUMMARY

In some embodiments, disclosed is a synthetic peptide 12 to 30 amino acids in length, wherein the peptide is an antagonist of chemokine receptor 3 (CXCR3) signaling, and wherein the synthetic peptide comprises at least 12 consecutive amino acids of any one of SEQ ID NOs: 5-24 and 28-29.

In additional embodiments, disclosed is a synthetic peptide 12 to 30 amino acids in length, wherein the peptide is an agonist of CXCR3 signaling, and wherein the synthetic peptide comprises at least 12 consecutive amino acids of any one of SEQ ID NOs: 7, 9, 14, 17, 19 and 35-42.

In other embodiments, disclosed is a synthetic polypeptide comprising the amino acid sequence of any one of SEQ ID NOs: 5-42 that is an agonist or antagonist of CXCR3 signaling.

Nucleic acid molecules and vectors encoding these synthetic polypeptides are also disclosed. Vector including these nucleic acids, and host cells transformed with these vectors are also provided. In addition, disclosed are pharmaceutical compositions that include the disclosed synthetic peptides, nucleic acid molecules, and vectors Described herein are interferon-γ-inducible protein 10 (IP-10) peptides, IP-10 peptide variants and in silico designed CXCR3 peptide agonists. The small peptides can be used for inhibiting pathological tissue remodeling and/or treating fibrosis in a subject, such as a subject with fibrosis of the heart, lung, liver, kidney or skin. These peptides also can be used for treating myocardial infarction, ischemia-reperfusion injury and/or cardiovascular disease in a subject.

Provided herein is a method of treating or inhibiting the development of fibrosis in a subject. In some embodiments, the method includes administering to the subject a therapeutically effective amount of a peptide or a composition that includes the peptide, wherein the peptide is an IP-10 peptide 12 to 30 amino acids in length and comprises the amino acid sequence of IP-10p (SEQ ID NO: 1) or a variant thereof, such as the peptide of SEQ ID NO: 2, SEQ ID NO: 3 and/or SEQ ID NO: 4. In other embodiments, the method includes administering to the subject a therapeutically effective amount of a peptide or a composition that includes the peptide, wherein the peptide is a CXCR3 agonist peptide that is 12 to 30 amino acids in length and comprises the amino acid sequence of any one of SEQ ID NOs: 7, 9, 14, 17, 19 and 35-42. In some embodiments, the peptide is administered in a composition that includes at least two peptides, such as 2 to 5 peptides. In some examples, the fibrosis is cardiac fibrosis. In other examples, the fibrosis is fibrosis of the lung, liver, kidney or skin.

Provided herein is a method of treating myocardial infarction, ischemia-reperfusion injury or a cardiovascular disease in a subject. In some embodiments, the method includes administering to the subject a therapeutically effective amount of a peptide or a composition that includes the peptide, wherein the peptide is an IP-10 peptide that is 12 to 30 amino acids in length and comprises the amino acid sequence of IP-10p (SEQ ID NO: 1) or a variant thereof, such as the peptide of SEQ ID NO: 2, SEQ ID NO: 3 and/or SEQ ID NO: 4. In other embodiments, the method includes administering to the subject a therapeutically effective amount of a peptide or a composition that includes the peptide, wherein the peptide is a CXCR3 agonist peptide that is 12 to 30 amino acids in length and comprises the amino acid sequence of any one of SEQ ID NOs: 7, 9, 14, 17, 19 and 35-42. In some embodiments, the peptide is administered in a composition that includes at least two peptides, such as 2 to 5 peptides. In some examples, the subject has suffered from a myocardial infarction within the last 48 hours or within the last 24 hours. In some examples, the cardiovascular disease is heart failure, coronary artery disease or aortic aneurysm.

Peptides designed in silico to bind CXCR3 and/or ligands of CXCR3 and inhibit CXCR3 signaling are described. IP-10 peptides that activate CXCR3 are also described. The disclosed peptides can be used to treat the underlying pathology associated with cardiovascular diseases, such as myocarditis and atherosclerosis.

Small synthetic peptides that are antagonists of CXCR3 signaling are disclosed. In some embodiments, the peptides are 12 to 30 amino acids in length. In some examples, the peptides include at least 12 consecutive amino acids of any one of SEQ ID NOs: 7, 9, 14, 17, 19 and 35-42. Compositions that include a synthetic peptide disclosed herein are also provided. In some embodiments, the compositions include more than one peptide, such as 2 to 5 of the disclosed peptides. In some embodiments, the compositions include one or more IP-10 peptides.

Also provided is an in vitro method of inhibiting CXCR3 signaling in a cell by contacting the cell with one or more synthetic peptides or a composition disclosed herein.

Further provided is a method of inhibiting CXCR3 signaling in a subject by administering to the subject one or more synthetic peptides or a composition disclosed herein.

Methods of treating myocarditis or atherosclerosis in a subject by administering one or more synthetic peptides or a composition disclosed herein are further described. In some embodiments, the synthetic peptide includes comprises at least 12 consecutive amino acids of any one of SEQ ID NOs: 5-24 and 28-29. In other embodiments, the synthetic polypeptide includes, or consists of, any one of SEQ ID NOs: 5-24 and 28-29.

The foregoing and other objects, features, and advantages of the disclosure will become more apparent from the following detailed description, which proceeds with reference to the accompanying figures.

BRIEF DESCRIPTION OF THE DRAWINGS

FIG. 3A), collagen type I alpha 1 chain (COL1A1.

(FIG. 5C) Fibroblasts treated with IP-10-3 peptide (100 ng/mL) in the presence of TGF-β demonstrated a reduction in migration rate compared to TGF-β-treated cells. Treatment with 100 ng/mL IP-10-1 (FIG. 5A) or IP-10-2 (FIG. 5) peptide did not affect the TGF-β-mediated induction in migration. Mean+/−SEM are shown in the graph.

SEQUENCE LISTING

Figure 1A:
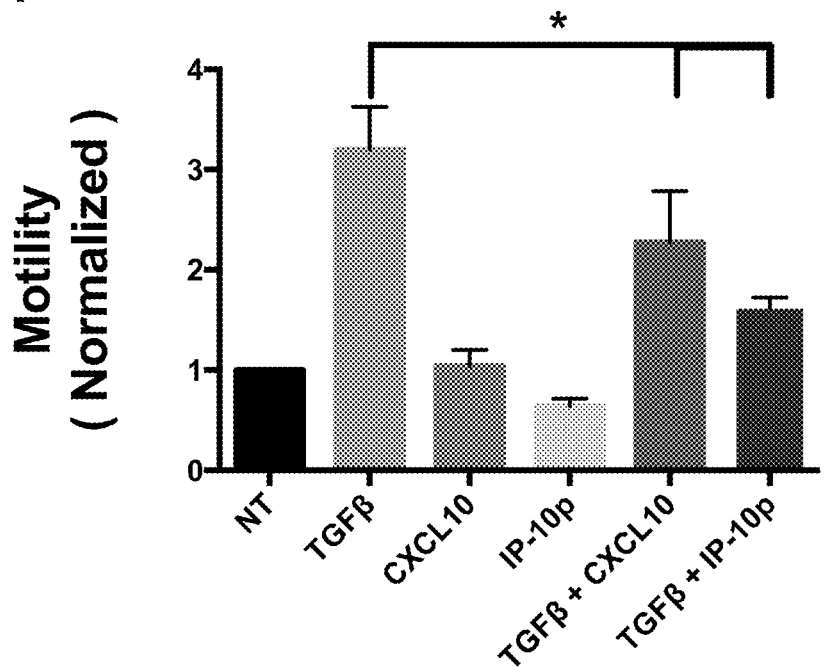
FIGS. 1A-1C: Effect of CXCL10 and IP-10 Peptide on growth factor induced cellular migration. CXCL10 & IP-10 Peptide inhibit migration following TGF-$\beta$ induction in cardiomyocytes (FIG. 1A) and cardiac fibroblasts (FIG. 1B). IP-10 Peptide inhibits cellular migration in TGF-$\beta$ induced co-cultures (FIG. 1C).
Figure 1B:
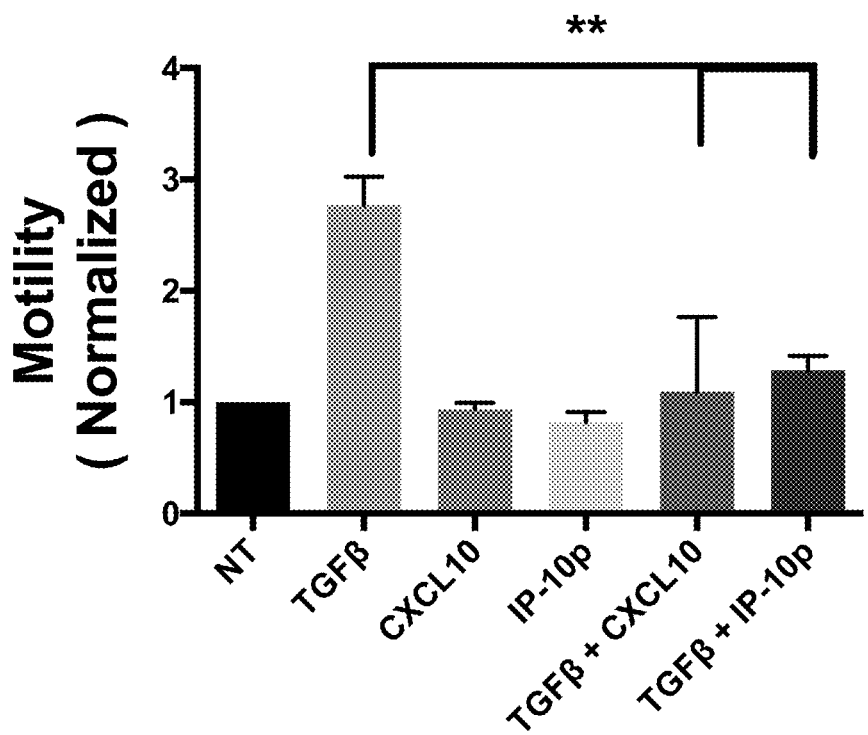
Figure 1C:
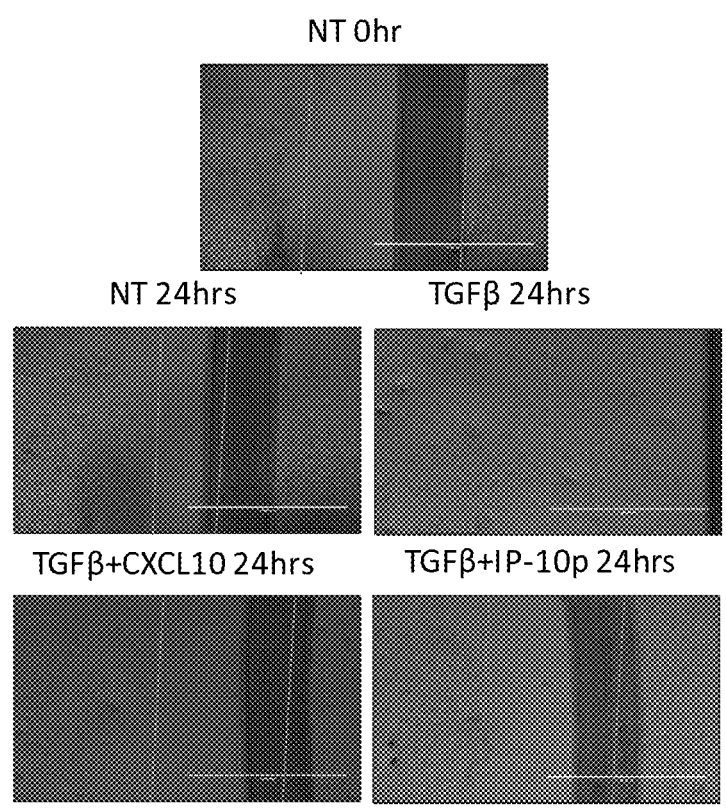
Figure 1C:
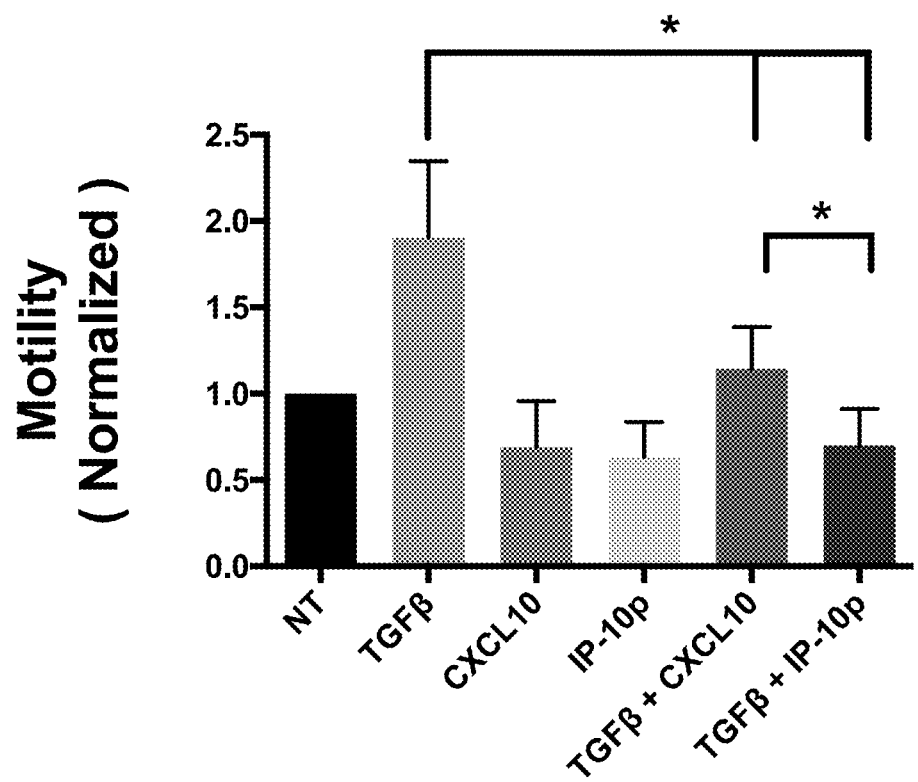

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 17, 2019, 11.1 KB, which is incorporated by reference herein. In the accompanying sequence listing:

SEQ ID NOs: 1-4 are the amino acid sequences of IP-10 peptides and variants.

SEQ ID NOs: 5-42 are the amino acid sequences of in silico designed peptides.

DETAILED DESCRIPTION

I. Abbreviations

α-SMA α-smooth muscle actin
CF cardiac fibroblast
COL1A1 collagen type I alpha 1 chain
CM cardiomyocyte
CTCF corrected total cell fluorescence
CXCL10 C-X-C chemokine ligand 10
CXCL11 C-X-C chemokine ligand 11
CXCR3 C-X-C chemokine receptor 3
CVB3 coxsackievirus B3
DAPI 4,6-diamidino-2-phenylindole
DCN decorin
ECM extracellular matrix
FBS fetal bovine serum
FN1 fibronectin 1
HF heart failure
IP-10 interferon-inducible protein 10
IPF idiopathic pulmonary fibrosis
MI myocardial infarction
SSc systemic sclerosis
TGF-β transforming growth factor β
TNC tenascin C II. Terms and Methods Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: The introduction of a composition (such as a protein or peptide) into a subject by a chosen route. For example, if the chosen route is intravenous, the composition is administered by introducing the composition into a vein of the subject. Exemplary routes of administration include, but are not limited to, injection (such as intraocular, subcutaneous, intramuscular, intradermal, intraperitoneal, and intravenous), oral, intraductal, sublingual, transdermal, intranasal, topical, inhalation routes and via a medical implant.

Agonist: A drug or molecule (such as a peptide) that promotes the activity or function of another drug or molecule. For example, an agonist of a receptor is a molecule that enhances activity (such as signaling activity) of the receptor. In some embodiments of the present disclosure, the "CXCR3 agonist" is a peptide that binds CXCR3 and enhance its signaling activity.

Antagonist: A drug or molecule (such as a peptide) that interferes with or inhibits the action or function of another drug or molecule. For example, an antagonist of a receptor is a molecule that inhibits activity (such as signaling activity) of the receptor. As used herein, an "antagonist of CXCR3 signaling" refers to a peptide that interferes with the signaling activity mediated by CXCL10 and/or CXCR3. In some examples, the antagonistic peptides disclosed herein bind CXCL10 or CXCL11 and prevent binding of these proteins to their receptor CXCR3. In other examples, the antagonistic peptides bind CXCR3 and prevent binding of one or more ligands for CXCR3.

Aortic aneurysm: An enlargement of the aorta to greater than 1.5 times its normal size. Aortic aneurysms cause weakness of the aortic wall and increase the risk of aortic rupture, which results in massive internal bleeding.

Atherosclerosis: A disease characterized by the progressive narrowing and hardening of an artery over time due to the build-up of plaque. In particular, in patients with atherosclerosis, deposits of yellowish plaques (atheromas) containing cholesterol, lipid material and lipophages are formed within the intima and inner media of large and medium-sized arteries. Severe atherosclerosis can result in coronary artery disease, stroke, peripheral artery disease and/or kidney dysfunction. Current treatments include cholesterol-lowering medications (such as statins), blood pressure lowering medications, and medications that reduce clotting (such as aspirin).

Cardiovascular disease: A class of diseases that involve the heart or blood vessels, including coronary artery disease (also known as ischemic heart disease and coronary heart disease), peripheral artery disease, cerebrovascular disease, renal artery stenosis, aortic aneurysm, stroke, heart failure, hypertensive heart disease, pulmonary heart disease, cardiac dysrhythmia, rheumatic heart disease, inflammatory heart disease (including myocarditis and endocarditis), cardiomyopathy, heart arrhythmia, congenital heart disease, valvular heart disease, congenital heart disease, aortic aneurysm, thromboembolic disease and venous thrombosis. The underlying cause of each particular cardiovascular disease varies, but for some diseases (for example, coronary artery disease, stroke and peripheral artery disease) it is primarily due to atherosclerosis, which is promoted by high blood pressure, smoking, diabetes, lack of exercise, obesity, high cholesterol and poor diet.

Conservative variants: "Conservative" amino acid substitutions are those substitutions that do not substantially affect or decrease an activity or antigenicity of a protein, such as an IP-10 peptide, a CXCR3 antagonist peptide or a CXCR3 agonist peptide. For example, the peptides of any one of SEQ ID NOs: 1-42 can include at most about 1, at most about 2, at most about 3, at most about 4, at most about 5, at most about 6, at most about 7 or at most about 8 conservative substitutions (such as 1, 2, 3, 4, 5, 6, 7 or 8) conservative substitutions, such as 1 to 3, 1 to 5 or 2 to 6 conservative substitutions, and retain biological activity, such as the ability to bind CXCR3, CXCR4, CXCL4, CXCL9, CXCL10 and/or CXCL11, and/or the ability to activate CXCR3. In particular examples, the peptide variants have no more than 3 conservative amino acid substitutions. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid. Non-conservative substitutions are those that reduce an activity or antigenicity.

Contacting: Placement in direct physical association; includes both in solid and liquid form.

Coronary artery disease: A group of diseases that include myocardial infarction, sudden cardiac death, stable angina and unstable angina. Coronary artery disease, also known as coronary heart disease and ischemic heart disease, is characterized by a reduction in blood flow and oxygen to the heart muscle due to atherosclerosis of the cardiac arteries.

Coxsackievirus: A non-enveloped, positive-sense single-stranded RNA virus belonging to the family Picornaviridae and the genus Enterovirus. Coxsackieviruses are divided into two groups, Group A and Group B, based on their pathogenicity. Group A viruses generally infect the skin and mucous membranes. However, Group B viruses typically infect the heart, pleura, pancreas and liver, causing myocarditis, pleurodynia, pericarditis and hepatitis.

CXCL10 (C-X-C chemokine ligand 10): A chemokine of the CXC subfamily and ligand for the receptor CXCR3. Binding of CXCL10 to CXCR3 results in pleiotropic effects, including stimulation of monocytes, natural killer and T-cell migration, modulation of adhesion molecule expression, and inhibition of vessel formation. CXCL10 is also known as interferon-γ-inducible 10 kDa protein (IP-10).

CXCR3 (C-X-C chemokine receptor 3): A G protein-coupled receptor with selectivity for four chemokines, CXCL4, CXCL9, CXCL10 and CXCL11. Binding of chemokines to CXCR3 induces signaling and cellular responses that are involved in leukocyte trafficking, most notably integrin activation, cytoskeletal changes and chemotactic migration. Alternatively spliced transcript variants encoding different isoforms have been found for this gene. One of the isoforms (CXCR3-B) shows high affinity binding to chemokine CXCL4.

Fibrosis: A condition associated with the thickening and scarring of connective tissue. Often, fibrosis occurs in response to an injury, such as from a disease or condition that damages tissue. Fibrosis is an exaggerated wound healing response that when severe, can interfere with normal organ function. Fibrosis can occur in almost any tissue of the body, including in the lung (pulmonary fibrosis, cystic fibrosis, radiation-induced lung injury), liver (cirrhosis, biliary atresia), heart (arterial fibrosis, endomyocardial fibrosis, prior myocardial infarction), brain, skin (scleroderma, sclerosis), kidney, joints and intestine (Crohn's disease).

Influenza virus: A segmented negative-strand RNA virus that belongs to the Orthomyxoviridae family. There are three types of influenza viruses, influenza A, influenza B and influenza C viruses. Influenza A viruses can be classified into subtypes based on allelic variations in antigenic regions of two genes that encode surface glycoproteins, namely, hemagglutinin (HA) and neuraminidase (NA), which are required for viral attachment and cellular release. There are currently 18 different influenza A virus HA antigenic subtypes (H1 to H18) and 11 different influenza A virus NA antigenic subtypes (N1 to N11). H1-H16 and N1-N9 are found in wild bird hosts and may be a pandemic threat to humans. H17-H18 and N10-N11 have been described in bat hosts and are not currently thought to be a pandemic threat to humans. Specific examples of influenza A virus include, but are not limited to: H1N1, H1N2, H1N7, H2N2, H2N1, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6 and H14N5.

Heart failure: A disease resulting from the inability of the heart to pump blood in sufficient quantities to meet the body's requirements. Common causes of heart failure include coronary heart disease, previous myocardial infarction, high blood pressure, atrial fibrillation, valvular heart disease, excess alcohol use, infection and cardiomyopathy. There are two main types of heart failure—heart failure due to left ventricular dysfunction and heart failure with normal ejection fraction—depending on whether the ability of the left ventricle to contract is affected or the heart's ability to relax is affected.

Ischemia: A vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply.

Ischemia-reperfusion injury: Tissue damage caused by the return of blood supply after a period of ischemia or lack of oxygen. The restoration of blood flow results in inflammation and oxidative damage through the induction of oxidative stress.

Isolated: An "isolated" or "purified" biological component (such as a nucleic acid or peptide) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term.

Myocardial infarction (MI): A condition that occurs when blood flow decreases or stops to a part of the heart, causing damage to the heart muscle. MI is also known as "heart attack." Most MIs occur due to coronary artery disease. Risk factors for MI include high blood pressure, smoking, diabetes, lack of exercise, obesity, high cholesterol and poor diet.

Myocarditis: Inflammation of the heart muscle (myocardium). Myocarditis is often caused by viruses or other infectious organisms, such as bacteria, parasites, or fungi, but can also result from use of particular medications, drugs, chemicals, and radiation. Certain diseases and disorders, such as autoimmune disorders, can also cause myocarditis. Symptoms of myocarditis include shortness of breath, chest pain and irregular heartbeat.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peptide or polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide," "peptide," or "protein" as used herein are intended to encompass any amino acid sequence and include modified sequences such as glycoproteins. The terms "polypeptide" and "peptide" are specifically intended to cover naturally occurring proteins, as well as those which are recombinantly or synthetically produced.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the peptides herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. For topical application to the eye, agents can be mixed, for example, with artificial tears and other emulsions.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a particular polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 90%, 95%, 96%, 97%, 98% or 99% sequence identity counted over the full length alignment with the amino acid sequence of the polypeptide using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Signaling (Cell): A biochemical pathway induced in a cell, such as by a mechanical disruption or the binding of a ligand to its receptor. Signaling molecules include lipids, phospholipids, proteins, glycoproteins, amino acids and monoamines.

Subject: Living multi-cellular vertebrate organisms, a category that includes both human and veterinary subjects, including human and non-human mammals. In some examples, the subject suffers from fibrosis, a cardiovascular disease, myocardial infarction, ischemia-reperfusion injury, myocarditis or atherosclerosis.

Synthetic: Produced by artificial means in a laboratory, for example a synthetic nucleic acid or peptide can be chemically synthesized in a laboratory.

Therapeutically effective amount: A quantity of a specified agent (such as a CXCR3 antagonist peptide or a CXCR3 agonist peptide) sufficient to achieve a desired effect in a subject, cell or culture being treated with that agent. In some embodiments, the therapeutically effective amount is the amount of peptide necessary to inhibit CXCR3 signaling. In other embodiments, the therapeutically effective amount is the amount of peptide sufficient to treat myocarditis or atherosclerosis in a subject.

*Trypanosoma cruzi*: A parasitic protozoan that causes Chagas disease (also known as American trypanosomiasis). *T. cruzi* is commonly spread to human and other mammals by blood-sucking insects of the subfamily Triatominae. This parasite can also be spread through blood transfusion, organ transplantation, eating contaminated food and vertical transmission (mother to fetus).

Virus: A microorganism that cannot replicate outside of a living cell. Viruses have a nucleoprotein structure consisting of DNA or RNA (or both DNA and RNA), surrounded by a protein capsid or nucleocapsid. Some viruses further possess a lipid envelope.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Antagonist Peptides (CXCR3)

Peptides developed using an in silico prediction-based functional peptide strategy were designed to directly bind CXCR3 or ligands of CXCR3 to inhibit CXCR3 signaling, such as CXCL10-CXCR3 signaling or CXCL11-CXC3 signaling. The disclosed peptides can be used to treat the underlying pathology associated with cardiovascular diseases, such as myocarditis and atherosclerosis.

Provided are synthetic peptides 12 to 30 amino acids in length. These peptides are antagonists of CXCR3 signaling. In some embodiments, the peptides are 13 to 28, 14 to 26, or 15 to 25 amino acids in length. In some examples, the peptides are 12, 13, 14, 15, 16, 17, 18, 19, 20, 21, 22, 23, 24, 25, 26, 27, 28, 29 or 30 amino acids in length.

In some embodiments, the synthetic peptide comprises at least 12 consecutive amino acids of any one of SEQ ID NOs: 5-24 and 28-29 and is an antagonist of CXCR3 signaling. In some examples, the synthetic peptide comprises at least 13, at least 14, at least 15, at least 16, at least 17, at least 18, at least 19, at least 20, at least 21, at least 22, at least 23, or at least 24 consecutive amino acids of any one of SEQ ID NOs: 5-24 and 28-29. In particular examples, the amino acid sequence of the synthetic peptide comprises or consists of any one of SEQ ID NOs: 5-24 and 28-29.

In some embodiments, the synthetic peptide comprises an amino acid sequence having 1, 2, 3, 4, 5, 6, 7 or 8 conservative amino acid substitutions relative to any one of SEQ ID NOs: 5-24 and 28-29, and is an antagonist of CXCR3 signaling. In some examples, the synthetic peptide comprises an amino acid sequence having no more than 3, no more than 2 or no more than 1 conservative amino acid substitution relative to any one of SEQ ID NOs: 5-24 and 28-29. The polypeptide can include, or consist of, any one of SEQ ID NOs: 5-24 and 28-29.

In some embodiments, the synthetic peptides comprise at least one chemical modification. In some examples, the peptide comprises polyethylene glycol (PEG), one or more D-amino acids (d-AA), N-acetylation, lipidization, or B12 conjugation. In other examples, the peptide is cyclized.

In some embodiments, the synthetic peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

Also provided are compositions that include more than one synthetic peptide disclosed herein, such as 2-5 peptides, for example 1, 2, 3, 4, or 5 peptides. In some embodiments, the composition includes a pharmaceutically acceptable carrier.

Methods of inhibiting CXCR3 signaling in a subject are also described. In some embodiments, the method includes administering to the subject a synthetic peptide or composition disclosed herein.

IV. Agonist Peptides (CXCR3)

Peptides developed using an in silico prediction-based functional peptide strategy were designed to directly bind CXCR3 or ligands of CXCR3 and increase CXCR3 signaling. The disclosed peptides can be used to treat myocardial infarction, ischemia-reperfusion injury, or a cardiovascular disease. The disclosed peptides can be used to treat, or inhibit the development of, fibrosis.

Provided are synthetic peptides 12 to 30 amino acids in length. These peptides are agonists of CXCR3 signaling. In some embodiments, the peptides are 13 to 28, 14 to 26, or 15 to 25 amino acids in length. In some examples, the peptides are 12, 13, 14, 15, 16, 17, 18, 19, 20, 21, 22, 23, 24, 25, 26, 27, 28, 29 or 30 amino acids in length.

In some embodiments, the synthetic peptide comprises at least 12 consecutive amino acids of any one of SEQ ID NOs: 7, 9, 14, 17, 19 and 35-42, and is an antagonist of CXCR3 signaling. In some examples, the synthetic peptide comprises at least 13, at least 14, at least 15, at least 16, at least 17, at least 18, at least 19, at least 20, at least 21, at least 22, at least 23, or at least 24 consecutive amino acids of any one of SEQ ID NOs: 7, 9, 14, 17, 19 and 35-42. In particular examples, the amino acid sequence of the synthetic peptide comprises or consists of any one of SEQ ID NOs: 7, 9, 14, 17, 19 and 35-42.

In some embodiments, the synthetic peptide comprises an amino acid sequence having 1, 2, 3, 4, 5, 6, 7 or 8 conservative amino acid substitutions relative to any one of SEQ ID NOs: 7, 9, 14, 17, 19 and 35-42, and is an agonist of CXCR3 signaling. In some examples, the synthetic peptide comprises an amino acid sequence having no more than 3, no more than 2 or no more than 1 conservative amino acid substitution relative to any one of SEQ ID NOs: 7, 9, 14, 17, 19 and 35-42. The polypeptide can include, or consist of, any one of SEQ ID NOs: 7, 9, 14, 17, 19 and 35-42.

In some embodiments, the synthetic peptides comprise at least one chemical modification. In some examples, the peptide comprises polyethylene glycol (PEG), one or more D-amino acids (d-AA), N-acetylation, lipidization, or B12 conjugation. In other examples, the peptide is cyclized.

In some embodiments, the synthetic peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

Also provided are compositions that include more than one synthetic peptide disclosed herein, such as 2-5 peptides, for example 1, 2, 3, 4, or 5 peptides. In some embodiments, the composition includes a pharmaceutically acceptable carrier.

Methods of increasing CXCR3 signaling in a subject are also described. In some embodiments, the method includes administering to the subject a synthetic peptide or composition disclosed herein.

V. Antagonist Peptides (CXCR4)

Peptides developed using an in silico prediction-based functional peptide strategy were designed to directly bind CXCR4 and inhibit CXCR4 signaling, such as CXCL12-CXCR4 signaling. The disclosed peptides can be used to treat coronary artery disease, vascular injury due to restenosis from balloon angioplasty and stent implantation, reduce neointimal hyperplasia and the treatment of cancers such as non-Hodgkin's lymphomand and multiple myeloma.

Provided are synthetic peptides 12 to 30 amino acids in length. These peptides are antagonists of CXCR4 signaling. In some embodiments, the peptides are 13 to 28, 14 to 26, or 15 to 25 amino acids in length. In some examples, the peptides are 12, 13, 14, 15, 16, 17, 18, 19, 20, 21, 22, 23, 24, 25, 26, 27, 28, 29 or 30 amino acids in length.

In some embodiments, the synthetic peptide comprises at least 12 consecutive amino acids of any one of SEQ ID NOs: 25, 27, 30, 31 and 33 and is an antagonist of CXCR4 signaling. In some examples, the synthetic peptide comprises at least 13, at least 14, at least 15, at least 16, at least 17, at least 18, at least 19, at least 20, at least 21, at least 22, at least 23, or at least 24 consecutive amino acids of any one of SEQ ID NOs: 25, 27, 30, 31 and 33. In particular examples, the amino acid sequence of the synthetic peptide comprises or consists of any one of SEQ ID NOs: 25, 27, 30, 31 and 33.

In some embodiments, the synthetic peptide comprises an amino acid sequence having 1, 2, 3, 4, 5, 6, 7 or 8 conservative amino acid substitutions relative to any one of SEQ ID NOs: 25, 27, 30, 31 and 33 and is an antagonist of CXCR4 signaling. In some examples, the synthetic peptide comprises an amino acid sequence having no more than 3, no more than 2 or no more than 1 conservative amino acid substitution relative to any one of SEQ ID NOs: 25, 27, 30, 31 and 33. The polypeptide can include, or consist of, any one of SEQ ID NOs: 25, 27, 30, 31 and 33.

In some embodiments, the synthetic peptides comprise at least one chemical modification. In some examples, the peptide comprises polyethylene glycol (PEG), one or more D-amino acids (d-AA), N-acetylation, lipidization, or B12 conjugation. In other examples, the peptide is cyclized.

In some embodiments, the synthetic peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

Also provided are compositions that include more than one synthetic peptide disclosed herein, such as 2-5 peptides, for example 1, 2, 3, 4, or 5 peptides. In some embodiments, the composition includes a pharmaceutically acceptable carrier.

Methods of inhibiting CXCR4 signaling in a subject are also described. In some embodiments, the method includes administering to the subject a synthetic peptide or composition disclosed herein.

VI. Agonist Peptides (CXCR4)

Peptides developed using an in silico prediction-based functional peptide strategy were designed to directly bind CXCR4 increase CXCR4 signaling, such as CXCL12-CXCR4 signaling. The disclosed peptides can be used to treat neurodegenerative diseases such as Parkinson's and Alzheimer's disease. It be used post MI to reduce infarct size and increase cardiac function and a clotting agent due to its pro-thrombotic actions.

Provided are synthetic peptides 12 to 30 amino acids in length. These peptides are agonists of CXCL12-CXCR4 signaling. In some embodiments, the peptides are 13 to 28, 14 to 26, or 15 to 25 amino acids in length. In some examples, the peptides are 12, 13, 14, 15, 16, 17, 18, 19, 20, 21, 22, 23, 24, 25, 26, 27, 28, 29 or 30 amino acids in length.

In some embodiments, the synthetic peptide comprises at least 12 consecutive amino acids of any one of SEQ ID NOs: 26, 27, 32, and 34, and is an agonist of CXCL12-CXCR4. In some examples, the synthetic peptide comprises at least 13, at least 14, at least 15, at least 16, at least 17, at least 18, at least 19, at least 20, at least 21, at least 22, at least 23, or at least 24 consecutive amino acids of SEQ ID NOs: 26, 27, 32, and 34. In particular examples, the amino acid sequence of the synthetic peptide comprises or consists of any one of SEQ ID NOs: 26, 27, 32, and 34.

In some embodiments, the synthetic peptide comprises an amino acid sequence having 1, 2, 3, 4, 5, 6, 7 or 8 conservative amino acid substitutions relative to any one of SEQ ID NOs: 26, 27, 32, and 34, and is an agonist of CXCL12-CXCR4. In some examples, the synthetic peptide comprises an amino acid sequence having no more than 3, no more than 2 or no more than 1 conservative amino acid substitution relative to any one of SEQ ID NOs: 26, 27, 32, and 34. The polypeptide can include, or consist of, any one of SEQ ID NOs: 26, 27, 32, and 34.

In some embodiments, the synthetic peptides comprise at least one chemical modification. In some examples, the peptide comprises polyethylene glycol (PEG), one or more D-amino acids (d-AA), N-acetylation, lipidization, or B12 conjugation. In other examples, the peptide is cyclized.

In some embodiments, the synthetic peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

Also provided are compositions that include more than one synthetic peptide disclosed herein, such as 2-5 peptides, for example 1, 2, 3, 4, or 5 peptides. In some embodiments, the composition includes a pharmaceutically acceptable carrier.

Methods of increasing CXCL12-CXCR4 signaling in a subject are also described. In some embodiments, the method includes administering to the subject a synthetic peptide or composition disclosed herein.

VII. Nucleic Acids and Vectors

Polynucleotides include DNA, cDNA and RNA sequences which encode an agonist peptide or antagonist peptide of interest, as disclosed herein. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

Nucleic acid molecules encoding agonist peptide or antagonist peptide can readily be produced by one of skill in the art, using the amino acid sequences provided herein, and the genetic code. Nucleic acid sequences encoding agonist peptide or antagonist peptide can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. Exemplary nucleic acids including sequences encoding the agonist peptide or antagonist peptide can be prepared by cloning techniques.

A nucleic acid encoding an agonist peptide or antagonist peptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., PCR Technology, (Stockton Press, N Y, 1989). Polynucleotides also can be isolated by screening genomic or cDNA libraries with probes selected from the sequences of the desired polynucleotide under stringent hybridization conditions.

In the context of the compositions and methods described herein, a nucleic acid sequence that encodes an agonist peptide or antagonist peptide, such as described above, is incorporated into a vector capable of expression in a host cell, using established molecular biology procedures. For example nucleic acids, such as cDNAs, that encode an agonist peptide or antagonist peptide can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Exemplary procedures sufficient to guide one of ordinary skill in the art through the production of vector capable of expression in a host cell (such as an adenoviral vector) that includes a polynucleotide sequence that encodes an agonist peptide or antagonist peptide can be found for example in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

Typically, a polynucleotide sequence encoding an agonist peptide or antagonist peptide is operably linked to transcriptional control sequences including, for example a promoter and a polyadenylation signal. A promoter is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, and promoters specific for keratinocytes, and epithelial cells.

The promoter can be either inducible or constitutive. An inducible promoter is a promoter which is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2 kb, HSP70, proliferin, tumor necrosis factor, or thyroid stimulating hormone gene promoter.

Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

The polynucleotides encoding an agonist peptide or antagonist peptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

Viral vectors can also be prepared encoding the agonist peptide or antagonist peptide. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217, 879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding an agonist peptide or antagonist peptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus, yeast and the like.

Adenovirus vectors (Ad) vectors can be produced that encode an agonist peptide or antagonist peptide and are of use in the methods disclosed herein. These vectors are of use in the methods disclosed herein, including replication competent, replication deficient, gutless forms thereof, and adeno-associated virus (AAV) vectors. Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone.

VIII. Pharmaceutical Compositions

The agonist peptide or antagonist peptide, or a polynucleotide encoding the agonist peptide or antagonist peptide described herein can be formulated in a variety of ways depending on the location and type of disease to be treated. Pharmaceutical compositions are thus provided for both local use (for example, topical or within a stent), as well as for systemic use.

The subject can be any subject, such as a mammalian subject. Therefore, the disclosure includes within its scope pharmaceutical compositions comprising at least one agonist peptide or antagonist peptide, or a polynucleotide encoding the agonist peptide or antagonist peptide, formulated for use in human or veterinary medicine. Any of these compositions are of use in the methods disclosed herein.

Compositions are provided that include the peptides of SEQ ID NOs: 25-27 and 30-34, or nucleic acids molecules encoding these peptides. Compositoisn are provided that include more than one of these peptides. Compositions are provided that include at least one IP-10 peptide and at least one CXCR3 agonist peptide. Compositions are provided that include more than one agonist peptide, such as 1, 2, 3, 4, 5, 6, 7, 8, 9, or 10 different agonist peptides. Compositions are provided that include more than one antagonist peptide, such as 2, 3, 4, 5, 6, 7, 8, 9, or 10 antagonist peptides.

The agonist peptide or antagonist peptide and nucleic acids encoding SLU the agonist peptide or antagonist can be administered ex vivo (such as to a cell) or in vivo to a subject. Generally, it is desirable to prepare the compositions as pharmaceutical compositions appropriate for the intended application. Accordingly, methods for making a medicament or pharmaceutical composition containing the agonist peptide or antagonist peptide, nucleic acids, or vectors described above are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

Therapeutic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed agonist peptide or antagonist peptide, or nucleic acid encoding the agonist peptide or antagonist peptide, can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of agonist peptide or antagonist peptide, nucleic acid, or dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the vectors or viruses in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

Administration of therapeutic compositions can be by any common route as long as the target tissue is available via that route. This includes oral, nasal, ocular, buccal, or other mucosal (such as rectal or vaginal) or topical administration. Alternatively, administration will be by orthotopic, intradermal, subcutaneous, intramuscular, intraperitoneal, or intravenous injection routes. In some embodiments, the agonist peptide or antagonist peptide or the polynucleotide encoding the agonist peptide or antagonist peptide is formulated for administration to a lesion, such as in a stent or for other local administration. Pharmaceutical compositions are usually administered that include physiologically acceptable carriers, buffers or other excipients. Pharmaceutical compositions that include an agonist peptide or antagonist peptide, and/or a polynucleotide encoding the agonist peptide or antagonist peptide, as an active ingredient, can be formulated with an appropriate solid or liquid carrier, depending upon the particular mode of administration chosen.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art. Implants can also be employed.

The pharmaceutical compositions that include an agonist peptide or antagonist peptide, or a nucleic acid encoding the agonist peptide or antagonist peptide, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The agonist peptide or antagonist peptide, or a nucleic acid encoding the agonist peptide or antagonist peptide can be included in an inert matrix for either topical application or injection. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including an agonist peptide or antagonist peptide, or a nucleic acid encoding the agonist peptide or antagonist peptide can be applied topically or can be injected for systemic administration. In some formulations, the agonist peptide or antagonist peptide, or a nucleic acid encoding the agonist peptide or antagonist peptide is slowly released over time as the liposome capsule degrades. These formulations, and others, provide advantages of a slow release drug delivery system, allowing the subject to be exposed to a substantially constant concentration. In one example, the agonist peptide or antagonist peptide, or a nucleic acid encoding the agonist peptide or antagonist peptide, can be dissolved in an organic solvent such as DMSO or alcohol as previously described and contain a polyanhydride, poly(glycolic) acid, poly(lactic) acid, or polycaprolactone polymer.

IX. Methods of Treating Fibrosis

Fibrosis is a pathological process by which scar-like tissue replaces healthy tissue. Organ fibrosis can occur in localized diseases, such as idiopathic pulmonary fibrosis (IPF) or in systemic diseases like systemic sclerosis (SSc). When fibrosis takes place in the lung, the resulting tissue is suboptimal for transporting oxygen into the bloodstream, resulting in symptoms that progress from shortness of breath to acute respiratory failure in patients with IPF and systemic fibrotic diseases such as systemic sclerosis SSc. The prognosis for IPF patients is dismal, with a 60-80% 5-year mortality rate. Currently, there are no approved therapeutics for IPF that reverse fibrosis. As a result, IPF remains a significant burden on the healthcare system, ranking as the most common indication for lung transplantation in the United States. Similarly, fibrosis of the skin in SSc and other disorders leads to stiffened skin, pain and decreased quality of life for patients.

There are no currently approved drugs that have been shown to reverse lung or skin fibrosis. Thus, the only curative treatment for pulmonary fibrosis is lung transplantation—an expensive approach that is limited by both the number of available donor lungs and recipient eligibility. Other treatment options include oxygen therapy, use of steroids, and palliative care for advanced disease. Two recently approved drugs, Pirfenidone and Nintedanib, were shown to modestly decrease rate of progression in IPF. However, these drugs were not effective in some patient subsets. The mechanism of action of Pirfenidone is not completely understood, but it is known to inhibit the production and activity of TGFβ and can diminish inflammation. Nintedanib acts by inhibiting growth factor receptors involved in the pathogenesis of fibrosis.

Current treatment for dermal fibrosis includes injection of corticosteroids into areas of fibrosis (hypertrophic scars and keloids) and surgical removal. Steroid injections cause atrophy of surrounding tissue, including fat and muscle, and keloids frequently recur following surgical resection. In SSc patients, immunosuppressive agents are used with low efficacy.

Previous studies have shown that CXCR3 and its natural ligands inhibit the pathogenesis of fibrosis by at least two mechanisms. Acting through its receptor CXCR3, CXCL10 inhibits activity of the pro-fibrotic growth factor TGFβ and stops angiogenesis. The peptides disclosed herein are designed to act as agonists for CXCR3 in a similar fashion to these endogenous ligands.

Previous studies have determined that the ligand C-X-C motif chemokine 10 (CXCL10), also known as interferon gamma-induced protein 10 (IP-10), is an inhibitor of fibroblast function. CXCL10 is secreted by several cell types, including fibroblasts. Recent studies have demonstrated the critical role of CXCL10 in the post-MI remodeling response using CXCL10−/− mice. In these studies, the lack of CXCL10 resulted in significantly more infiltrating leukocytes, macrophage, and aSMA-expressing myofibroblasts into the infarct. This increased cellular infiltration promoted a larger infarction and dilation at day 7 and significantly more systolic dysfunction at day 28. CXCL10 was found to inhibit basic fibroblast growth factor (bFGF)-induced migration of fibroblasts but did not appear to alter fibroblast proliferation or apoptosis. Subsequent studies identified that the CXCL10 actions in the infarcted heart and isolated cardiac fibroblasts were mediated through proteoglycans. Together these studies indicate a protective role for CXCL10, which includes the attenuation of cardiac fibroblast activation and collagen secretion. In addition, CXCL10 preserved cardiac function during the post-MI remodeling process.

A CXCL10 peptide consisting of the α-helical domain (residues 77-98) that mimics the action of CXCL10 on dermal endothelial cells via CXCR3 has been described (PCT Publication Nos. WO 2013/032853 and WO 2015/112505, incorporated herein by reference). Specifically, this peptide, referred to as IP-10p, activates the CXCR3B isoform that inhibits migration and proliferation in various cell types. In the heart, however, evidence suggests that CXCL10 signals through an alternative CXCR3-independent pathway to reduce fibrosis after MI. Although IP-10p has been shown to be able to inhibit angiogenesis, it has not been tested in anti-fibrotic applications or in cardiac cells. The study disclosed herein demonstrates for the first time that IP-10p exhibits an anti-fibrotic activity in cardiac cells in TGFβ1-induced fibrotic conditions. Further, the present disclosure demonstrates that α-helix IP-10p is capable of signaling in a CXCR3-independent manner, similar to the whole CXCL10 protein. The results disclosed herein demonstrate the therapeutic potential of IP-10p in attenuating post-MI fibrosis.

Small peptides that act on the chemokine receptor CXCR3 were designed in silico. Naturally occurring ligands of CXCR3, such as CXCL10 and CXCL11, are potent anti-fibrotic chemokines. The small peptides were designed to inhibit and reverse the pathogenesis of fibrosis through multiple mechanisms. In particular, the peptides were designed to have the ability to simultaneously target two activities that contribute to fibrosis: (1) the activity of pro-fibrotic TGFβ and (2) increased angiogenesis. Activation of CXCR3 by natural ligands has potent anti-angiogenic effects in multiple tissues. In addition, it has been determined that CXCL10 inhibits the effects of TGFβ, a factor considered to be a major contributor to fibrosis. TGFβ increases production of extracellular matrix components, tenascin, and alpha smooth muscle actin by fibroblast cells. Full-length CXCL10 inhibits these effects of TGFβ.

To generate the small peptides, an adaptive algorithm for in silico prediction-based functional peptide design was used to identify multiple small peptides that mimic the functions of full-length CXCR3 ligands. These peptides were specifically designed to act through CXCR3, thereby inhibiting the effects of TGFβ and halting angiogenesis and excessive tissue remodeling.

One challenge to developing treatments for fibrotic diseases is the heterogeneity of patient populations. Especially in the case of SSc, the rate of disease progression is variable and difficult to predict. Along with genetic studies, this has led researchers to believe that SSc may actually represent multiple clinical subgroups. This heterogeneity also results in differential response of patients to therapeutics. The disclosed peptides are all designed to work through the CXCR3 receptor, but may have different magnitudes of response on angiostatic and anti-TGFβ pathways. Therefore, the disclosed peptides or combinations thereof can be tailored to individuals based on their disease need in a personalized medicine approach.

Provided herein is a method of treating or inhibiting the development of fibrosis in a subject. In some embodiments, the method includes administering to the subject a therapeutically effective amount of a peptide or a composition that includes the peptide, wherein the peptide is an IP-10 peptide that is 12 to 30 amino acids in length and comprises the amino acid sequence of IP-10p (SEQ ID NO: 1) or a variant thereof, such as the peptide of SEQ ID NO: 2, SEQ ID NO: 3 and/or SEQ ID NO: 4. In other embodiments, the method includes administering to the subject a therapeutically effective amount of a peptide or a composition that includes the peptide, wherein the peptide is a CXCR3 agonist peptide that is 12 to 30 amino acids in length and comprises the amino acid sequence of any one of SEQ ID NOs: 1-4, 7, 9, 14, 17, 19 and 35-42.

Also provided is a method of inhibiting pathological tissue remodeling in a subject. In some embodiments, the method includes administering to the subject a therapeutically effective amount of a peptide or a composition that includes the peptide, wherein the peptide is an IP-10 peptide that is 12 to 30 amino acids in length and comprises the amino acid sequence of IP-10p (SEQ ID NO: 1) or a variant thereof, such as the peptide of SEQ ID NO: 2, SEQ ID NO: 3 and/or SEQ ID NO: 4. In other embodiments, the method includes administering to the subject a therapeutically effective amount of a peptide or a composition that includes the peptide, wherein the peptide is a CXCR3 agonist peptide that is 12 to 30 amino acids in length and comprises the amino acid sequence of any one of SEQ ID NO: 7, 9, 14, 17, 19 and 35-42.

In some embodiments of the disclosed methods, the peptide is 12 to 30 amino acids in length, such as 12 to 25, 13 to 17 or 14 to 16 amino acids in length. In some examples, the peptide is 12, 13, 14, 15, 16, 17, 18, 19, 20, 21, 22, 23, 24, 25, 26, 27, 28, 29 or 30 amino acids in length.

In some embodiments, the peptide comprises at least 12 consecutive amino acids of any one of SEQ ID NOs: 1-4, 7, 9, 14, 17, 19 and 35-42. In some examples, the peptide comprises at least 13, at least 14, at least 15, at least 16, at least 17, at least 18, at least 19, at least 20, at least 21, at least 22, at least 23, or at least 24 consecutive amino acids of any one of SEQ ID NOs: 1-4, 7, 9, 14, 17, 19 and 35-42. In particular examples, the amino acid sequence of the peptide comprises or consists of any one of SEQ ID NOs: 1-4, 7, 9, 14, 17, 19 and 35-42.

In some embodiments, the peptide comprises an amino acid sequence having 1, 2, 3, 4, 5, 6, 7 or 8 conservative amino acid substitutions relative to any one of SEQ ID NOs: 1-4, 7, 9, 14, 17, 19 and 35-42. In some examples, the synthetic peptide comprises an amino acid sequence having no more than 3, no more than 2 or no more than 1 conservative amino acid substitution relative to any one of SEQ ID NOs: 1-4, 7, 9, 14, 17, 19 and 35-42.

In specific examples, the amino acid sequence of the peptide comprises or consists of SEQ ID NO: 1, SEQ ID NO: 2, SEQ ID NO: 3 or SEQ ID NO: 4. In other specific examples, the amino acid sequence of the peptide comprises or consists of one of SEQ ID NOs: 7, 9, 14, 17, 19 and 35-42

In some embodiments, the peptide comprises at least one chemical modification. In some examples, the peptide comprises polyethylene glycol (PEG), one or more D-amino acids (d-AA), N-acetylation, lipidization, or B12 conjugation. In other examples, the peptide is cyclized.

In some embodiments, the peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

In some embodiments of the disclosed methods, the subject is administered a composition that includes the peptide. In some examples, the composition includes at least two peptides, such as 2 to 5 peptides, for example 1, 2, 3, 4, or 5 peptides. In some examples, the composition includes at least one IP-10 peptide and at least one CXCR3 agonist peptide. In particular examples, the composition includes one IP-10 peptide and one CXCR3 agonist peptide, or includes two IP-10 peptides and one CXCR3 peptide, or includes one IP-10 peptide and two CXCR3 peptides, or includes two IP-10 peptides and two CXCR3 peptides, or includes three IP-10 peptides and two CXCR3 agonist peptides, or includes two IP-10 peptides and three CXCR3 agonist peptides. In some embodiments, the composition includes a pharmaceutically acceptable carrier.

In some embodiments, the fibrosis is cardiac fibrosis. In some examples, the subject has suffered from a myocardial infarction.

In other embodiments, the fibrosis is fibrosis of the lung, liver, kidney or skin.

In some embodiments, the pathological tissue remodeling is in the heart, lung, liver, kidney or skin.

Also provided herein are IP-10 and CXCR3 agonist peptides. In some embodiments, the peptide is an IP-10 peptide that is 12 to 30 amino acids in length and comprises the amino acid sequence of IP-10p (SEQ ID NO: 1) or a variant thereof, such as the peptide of SEQ ID NO: 2, SEQ ID NO: 3 and/or SEQ ID NO: 4. In other embodiments, the peptide is a CXCR3 agonist peptide that is 12 to 30 amino acids in length and comprises the amino acid sequence of any one of SEQ ID NOs: 4-42.

In some embodiments, the peptide is 12 to 30 amino acids in length, such as 12 to 25, 13 to 17 or 14 to 16 amino acids in length. In some examples, the peptide is 12, 13, 14, 15, 16, 17, 18, 19, 20, 21, 22, 23, 24, 25, 26, 27, 28, 29 or 30 amino acids in length.

In some embodiments, the peptide comprises at least 12 consecutive amino acids of any one of SEQ ID NOs: 1-4, 7, 9, 14, 17, 19 and 35-42. In some examples, the peptide comprises at least 13, at least 14, at least 15, at least 16, at least 17, at least 18, at least 19, at least 20, at least 21, at least 22, at least 23, or at least 24 consecutive amino acids of any one of SEQ ID NOs: 1-4, 7, 9, 14, 17, 19 and 35-42. In particular examples, the amino acid sequence of the peptide comprises or consists of any one of SEQ ID NOs: 1-4, 7, 9, 14, 17, 19 and 35-42.

In some embodiments, the peptide comprises an amino acid sequence having 1, 2, 3, 4, 5, 6, 7 or 8 conservative amino acid substitutions relative to any one of SEQ ID NOs: 1-4, 7, 9, 14, 17, 19 and 35-42. In some examples, the synthetic peptide comprises an amino acid sequence having no more than 3, no more than 2 or no more than 1 conservative amino acid substitution relative to any one of SEQ ID NOs: 1-4, 7, 9, 14, 17, 19 and 35-42.

In some embodiments, the peptide comprises at least one chemical modification. In some examples, the peptide comprises polyethylene glycol (PEG), one or more D-amino acids (d-AA), N-acetylation, lipidization, or B12 conjugation. In other examples, the peptide is cyclized.

In some embodiments, the peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

Further provided are compositions that include at least two peptides disclosed herein, such as 2 to 5 peptides, for example 1, 2, 3, 4, or 5 peptides. In some examples, the composition includes at least one IP-10 peptide and at least one CXCR3 agonist peptide. In particular examples, the composition includes one IP-10 peptide and one CXCR3 agonist peptide, or includes two IP-10 peptides and one CXCR3 peptide, or includes one IP-10 peptide and two CXCR3 peptides, or includes two IP-10 peptides and two CXCR3 peptides, or includes three IP-10 peptides and two CXCR3 agonist peptides, or includes two IP-10 peptides and three CXCR3 agonist peptides. In some embodiments, the composition includes a pharmaceutically acceptable carrier.

Isolated nucleic acid molecules encoding a synthetic peptide disclosed herein are also provided. In some embodiments, the nucleic acid molecule is operably linked to a promoter. Further provided is a vector comprising a nucleic acid encoding a synthetic peptide.

X. Methods of Treating Cardiovascular Disease

After myocardial infarction (MI), a prominent feature of the post-infarction period is the upregulation of chemokines, which play a role in leukocyte trafficking during would healing. During the first 24 hours post-MI, CXCL10 is upregulated and acts as an angiostatic and anti-fibrotic chemokine to prevent premature neovascularization and fibrosis until the damaged myocardium is cleared of apoptotic and necrotic cells. The importance of CXCL10 has been reported in CXCL10−/− mice, which exhibit a greater inflammatory cell infiltration, reduced neo-angiogenesis and expanded scar formation. CXCL10 is also a circulating biomarker and predictor of acute MI and therefore may be used to monitor the CXCL10 therapies disclosed herein. The upregulation of CXCL10 mRNA six hours after reperfusion (in ischemia reperfusion injury), and between 24 and 48 hours in myocardial infarction injury, make CXCL10 agonists particularly amenable to therapy.

Therapeutic targeting of MI has historically focused on treating the acute occlusion (reperfusion therapy) and by beta-blockade to reduce renin-angiotensinaldosterone-system axis activity. However, efforts to alter post-MI remodeling have been limited to single targets, such as inhibiting extracellular matrix remodeling via matrix metalloprotein (MMP) inhibition or regenerating cardiomyocytes. In contrast to these single targets, enhancing CXCR3 signaling, such as CXCL10-CXCR3 signaling, post-MI enhances multiple important endpoints that are ongoing for weeks after MI. This includes reducing inflammation and fibrosis, which contribute to both systolic and diastolic dysfunction.

The present disclosure describes IP-10 peptides and CXCR3 and CXCR4 agonist peptides designed to enhance CXCL10-CXCR3, CXCL11-CXCRs and CXCL12-CXCR4 signaling, such as to treat a subject post-MI. Use of these small CXCL10 factors to revert the underlying pathology of a host of cardiovascular diseases is further described.

The present disclosure describes small peptides that act on the chemokine receptor CXCR3 and CXCR4 and their use for treating cardiovascular diseases, myocardial infarction and/or ischemia-reperfusion injury. Some of the proposed peptides are IP-10 peptides and variants thereof. The remaining peptides were specifically designed to activate CXCR3 and CXCR4 signaling. To generate these small peptides, an adaptive algorithm for in silico prediction-based functional peptide design was used to identify multiple small peptides that promote CXCR3 and CXCR4 signaling.

Provided herein is a method of treating myocardial infarction, ischemia-reperfusion injury or a cardiovascular disease in a subject. In some embodiments, the method includes administering to the subject a therapeutically effective amount of a peptide or a composition that includes the peptide, wherein the peptide is an IP-10 peptide that is 12 to 30 amino acids in length and comprises the amino acid sequence of IP-10p (SEQ ID NO: 1) or a variant thereof, such as the peptide of SEQ ID NO: 2, SEQ ID NO: 3 and/or SEQ ID NO: 4. In other embodiments, the method includes administering to the subject a therapeutically effective amount of a peptide or a composition that includes the peptide, wherein the peptide is a CXCR3 agonist peptide that is 12 to 30 amino acids in length and includes the amino acid sequence of any one of SEQ ID NOs: 7, 9, 14, 17, 19 and 35-42. In other embodiments, the peptide is a CXCR4 agonist peptide that is 12 to 30 amino acids in length and includes the amino acid sequence of any one of SEQ ID NOs: 32 and 34.

In some embodiments, the peptide is 12 to 30 amino acids in length, such as 12 to 25, 13 to 17 or 14 to 16 amino acids in length. In some examples, the peptide is 12, 13, 14, 15, 16, 17, 18, 19, 20, 21, 22, 23, 24, 25, 26, 27, 28, 29 or 30 amino acids in length.

In some embodiments, the peptide comprises at least 12 consecutive amino acids of any one of SEQ ID NOs: 1-42. In some examples, the peptide comprises at least 13, at least 14, at least 15, at least 16, at least 17, at least 18, at least 19, at least 20, at least 21, at least 22, at least 23, or at least 24 consecutive amino acids of any one of SEQ ID NOs: 1-4, 7, 9, 14, 17, 19, 32, 34 and 35-42. In particular examples, the amino acid sequence of the peptide comprises or consists of any one of SEQ ID NOs: 1-4, 7, 9, 14, 17, 19 and 35-42.

In some embodiments, the peptide comprises an amino acid sequence having 1, 2, 3, 4, 5, 6, 7 or 8 conservative amino acid substitutions relative to any one of SEQ ID NOs: 1-4, 7, 9, 14, 17, 19, 32, 34 and 35-42. In some examples, the synthetic peptide comprises an amino acid sequence having no more than 3, no more than 2 or no more than 1 conservative amino acid substitution relative to any one of SEQ ID NOs: 1-4, 7, 9, 14, 17, 19 and 35-42.

In some embodiments, the peptide comprises at least one chemical modification. In some examples, the peptide comprises polyethylene glycol (PEG), one or more D-amino acids (d-AA), N-acetylation, lipidization, or B12 conjugation. In other examples, the peptide is cyclized. In some embodiments, the peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

In some embodiments of the disclosed methods, the subject is administered a composition that includes the peptide. In some examples, the composition includes at least two peptides, such as 2 to 5 peptides, for example 1, 2, 3, 4, or 5 peptides. In some examples, the composition includes at least one IP-10 peptide and at least one CXCR3 agonist peptide. In particular examples, the composition includes one IP-10 peptide and one CXCR3 agonist peptide, or includes two IP-10 peptides and one CXCR3 peptide, or includes one IP-10 peptide and two CXCR3 peptides, or includes two IP-10 peptides and two CXCR3 peptides, or includes three IP-10 peptides and two CXCR3 agonist peptides, or includes two IP-10 peptides and three CXCR3 agonist peptides. In some embodiments, the composition includes a pharmaceutically acceptable carrier.

In some embodiments, the subject has suffered from a myocardial infarction within the last 48 hours, or within the last 24 hours.

In some embodiments, the method is a method of treating a cardiovascular disease, such as coronary artery disease, peripheral artery disease, cerebrovascular disease, renal artery stenosis, aortic aneurysm, stroke, heart failure, hypertensive heart disease, pulmonary heart disease, cardiac dysrhythmia, rheumatic heart disease, inflammatory heart disease, cardiomyopathy, heart arrhythmia, congenital heart disease, valvular heart disease, congenital heart disease, aortic aneurysm, thromboembolic disease or venous thrombosis. In particular examples, the cardiovascular disease is heart failure, coronary artery disease or aortic aneurysm. Also provided herein are IP-10 and CXCR3 agonist peptides. In some embodiments, the peptide is an IP-10 peptide that is 12 to 30 amino acids in length and comprises the amino acid sequence of IP-10p (SEQ ID NO: 1) or a variant thereof, such as the peptide of SEQ ID NO: 2, SEQ ID NO: 3 and/or SEQ ID NO: 4. In other embodiments, the peptide is a CXCR3 agonist peptide that is 12 to 30 amino acids in length and comprises the amino acid sequence of any one of SEQ ID NOs: 4-42.

In some embodiments, the peptide is 12 to 30 amino acids in length, such as 12 to 25, 13 to 17 or 14 to 16 amino acids in length. In some examples, the peptide is 12, 13, 14, 15, 16, 17, 18, 19, 20, 21, 22, 23, 24, 25, 26, 27, 28, 29 or 30 amino acids in length.

In some embodiments, the peptide comprises at least 12 consecutive amino acids of any one of SEQ ID NOs: 1-42. In some examples, the peptide comprises at least 13, at least 14, at least 15, at least 16, at least 17, at least 18, at least 19, at least 20, at least 21, at least 22, at least 23, or at least 24 consecutive amino acids of any one of SEQ ID NOs: 1-4, 7, 9, 14, 17, 19 and 35-42. In particular examples, the amino acid sequence of the peptide comprises or consists of any one of SEQ ID NOs: SEQ ID NOs: 1-4, 7, 9, 14, 17, 19 and 35-42.

In some embodiments, the peptide comprises an amino acid sequence having 1, 2, 3, 4, 5, 6, 7 or 8 conservative amino acid substitutions relative to any one of SEQ ID NOs: 1-4, 7, 9, 14, 17, 19 and 35-42. In some examples, the synthetic peptide comprises an amino acid sequence having no more than 3, no more than 2 or no more than 1 conservative amino acid substitution relative to any one of SEQ ID NOs: 1-4, 7, 9, 14, 17, 19 and 35-42.

In some embodiments, the peptide comprises at least one chemical modification. In some examples, the peptide comprises polyethylene glycol (PEG), one or more D-amino acids (d-AA), N-acetylation, lipidization, or B12 conjugation. In other examples, the peptide is cyclized.

In some embodiments, the peptide further includes a tag, such as such as an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

Further provided are compositions that include at least two peptides disclosed herein, such as 2 to 5 peptides, for example 1, 2, 3, 4, or 5 peptides. In some examples, the composition includes at least one IP-10 peptide and at least one CXCR3 agonist peptide. In particular examples, the composition includes one IP-10 peptide and one CXCR3 agonist peptide, or includes two IP-10 peptides and one CXCR3 peptide, or includes one IP-10 peptide and two CXCR3 peptides, or includes two IP-10 peptides and two CXCR3 peptides, or includes three IP-10 peptides and two CXCR3 agonist peptides, or includes two IP-10 peptides and three CXCR3 agonist peptides. In some embodiments, the composition includes a pharmaceutically acceptable carrier.

Isolated nucleic acid molecules encoding a synthetic peptide disclosed herein are also provided. In some embodiments, the nucleic acid molecule is operably linked to a promoter. Further provided is a vector comprising a nucleic acid encoding a synthetic peptide.

XI. Methods of Treating Myocarditis and Atherosclerosis

Recent discoveries have implicated the chemokine CXCL10 as a contributing factor to myocarditis. Multiple groups have reported that CXCL10 is significantly induced in the hearts of mice infected with coxsackievirus B3 (CVB3), the most dominant etiologic agent seen in the U.S. CXCL10 contributes to the massive inflammatory cell infiltrate, driving the pathogenesis of disease in these animal models. Interfering with CXCL10 (also known as interferon-inducible protein 10, IP-10) significantly reduced CVB3-mediated cardiac hypertrophy and serum CK-MB (a marker of cardiomyocyte damage by necrosis/apoptosis). Reduced CXCL10-mediated signaling resulted in increased survival rates and improved histopathology attributed to a blunted Th1 immune response. Reports have shown that CVB3 and influenza A induce CXCL10 expression through PAR-1 and TLR3 signaling cascade in cardiac fibroblasts. Other causes of myocarditis, including Chagas disease, which causes heart failure in about 30% of the 8 million patients infected with the parasite *Trypanosoma cruzi*, have a similar relationship between the CXCL10 genotype and intensity of myocarditis.

Therapies for myocarditis are largely clinical and based on symptoms and diagnosis of the underlying infection. With rare exception (for example, influenza virus), therapies for the offending pathogen do not exist, leading to more generalized anti-inflammatory therapies such as intravenous immunoglobulin (IVIg) and steroids, which have limited efficacy. Clinical management of heart failure using ventricular assist devices, ICD implantation, or heart transplantation and long-term immunosuppressive therapy is common. The use of peptide antagonists of CXCL10/CXCR3 provides a way to inhibit the cardiac damage induced by infections of multiple causes by directly blocking the underlying pathogenesis of disease without inhibiting the ability of the body to clear infection.

Further provided is an in vitro method of inhibiting CXCR3 signaling in a cell. In some embodiments, the method includes contacting the cell with a synthetic peptide or composition disclosed herein. In some examples, the cell is a cardiomyocyte or a cardiac fibroblast. In some examples, the synthetic peptide is a peptide comprising any one of SEQ ID NOs: 5-24 and 28-29, or a variant thereof.

Methods of inhibiting CXCR3 signaling in a subject are also described. In some embodiments, the method includes administering to the subject a synthetic peptide or composition disclosed herein. In some examples, the subject has a cardiovascular disease. In specific examples, the subject has myocarditis or atherosclerosis. In some examples, the synthetic peptide is a peptide comprising any one of SEQ ID NOs: 5-24 and 28-29, or a variant thereof. Any of the antagonist peptides disclosed herein are of use in these methods.

Also provided herein is a method of treating myocarditis in a subject by administering to the subject a therapeutically effective amount of a synthetic peptide or a composition disclosed herein. In some embodiments, the synthetic peptide is a peptide comprising any one of SEQ ID NOs: 5-24 and 28-29 or a variant thereof. In other embodiments, the synthetic peptide is a peptide comprising any one of SEQ ID NOs: 1-24 and 28-29, or a variant thereof. In some examples, the synthetic peptide comprises or consists of the amino acid sequence of SEQ ID NO: 40 or SEQ ID NO: 42. In some embodiments, the peptide or composition is administered intravenously, subcutaneously, orally, intranasally, or transdermally. In some examples, the peptide or composition is administered in a polymeric carrier, a nanoparticle, a multi-component carrier system, or via microneedle.

In some examples, the myocarditis in the subject is caused by a virus. Viruses that cause myocarditis include, but are not limited to, coxsackievirus, influenza virus, adenovirus, parvovirus B19, human immunodeficiency virus (HIV), rubella virus, poliovirus, cytomegalovirus, human herpesvirus 6 and hepatitis C virus. In specific examples herein, the virus is a coxsackievirus, such as CVB3, or an influenza virus, such as an influenza A virus.

In other examples, the myocarditis in the subject is caused by a bacterial infection. Bacteria that can cause myocarditis include, but are not limited to, *Brucella* species, *Corynebacterium* species, *Neisseria gonorrhoeae*, *Haemophilus influenza*, *Actinomyces* species, *Tropheryma whipplei*, *Vibrio cholera*, *Borrelia burgdorferi*, *Leptospira* species, *Rickettsia* species, and *Mycoplasma pnmoniae*.

In other examples, the myocarditis in the subject is caused by *Trypanosoma cruzi* or *Toxoplasma gondii*.

In yet other examples, the myocarditis is caused by an autoimmune disease, such as scleroderma, systemic lupus erythematosus, sarcoidosis, Chagas disease or Kawasaki disease; is triggered by an allergic reaction to a medication; or occurs in response to rejection after heart transplantation.

Myocarditis can also be caused by use or overuse of certain drugs, such as alcohol, anthracyclines, some types of chemotherapy, antipsychotics, clozapine and mephedrone, or by certain toxins or heavy metals.

Further provided is a method of treating atherosclerosis in a subject by administering to the subject a therapeutically effective amount of a synthetic peptide or a composition disclosed herein. In some embodiments, the peptide or composition is administered intravenously, subcutaneously, orally, intranasally, or transdermally. In some examples, the peptide or composition is administered in a polymeric carrier, a nanoparticle, a multi-component carrier system, or via microneedle.

Isolated nucleic acid molecules encoding a synthetic peptide disclosed herein are also provided. In some embodiments, the nucleic acid molecule is operably linked to a promoter. Further provided is a vector comprising a nucleic acid encoding a synthetic peptide.

The following examples are provided to illustrate certain particular features and/or embodiments. These examples should not be construed to limit the disclosure to the particular features or embodiments described.

EXAMPLES

Example 1: Small Peptides that Act on Chemokine Receptor CXCR3 and/or Modulate CXCL10-CXCR3 Signaling This example provides the sequences of 42 small peptides that function as CXCR3 agonists or antagonists. Four of the peptides are IP-10 peptides or variants thereof (SEQ ID NOs: 1-4). In addition, a series of small peptides (13 to 25 amino acids in length) were developed by in silico prediction-based functional peptide design to directly bind to CXCL4, CXCL9, CXCL10, CXCL11, CXCR3, CXCR4 or DPP4 (SEQ ID NOs: 5-42). The amino acid sequences of each peptide are provided in Table 1.

TABLE 1

| Name | SEQ ID NO: | Peptide Sequence |
|---|---|---|
| IP-10p | 1 | PESKAIKNLLKAVSKEMSKRSP |
| IP-10-1 | 2 | PESKVIKNLLKVASKERSKRSP |
| IP-10-2 | 3 | PESRVIKNLLRVVSKEKSRRSP |
| IP-10-3 | 4 | FAKAIKNFAKAVAKFA |
| CXCL10-1 | 5 | VRSTSISGGSISTSRV |
| CXCL10-2 | 6 | IIPASQFGGFPQSAPII |
| CXCL10-3 | 7 | FSPRVEIGGIEVRPSF |
| CXCL11-1 | 8 | FPMFKGGKFMPF |
| CXCL11-2 | 9 | RLSLSIGGISLSR |
| CXCR3LP2-1 | 10 | DDHKEINAGGANIEKHD |
| CXCR3LP2-2 | 11 | DDHKEIGGIEKHD |
| CXCL10-3-1 | 12 | FSPHVEIGGIEVHPSF |
| CXCL10-3-2 | 13 | FTPHVEIGGIEVHPTF |
| CXCL10-3-3 | 14 | FTHVEIGGIEVHTF |
| CXCL10-1MI | 15 | SISTSRVGGVRSTSIS |
| CXCL10-2MI | 16 | FPQSAPIGGIIPASQF |
| CXCL10-3MI | 17 | IEVRPSFGGFSPRVEI |
| CXCL11-1MI | 18 | KFMPFGGFPMFK |
| CXCL11-2MI | 19 | IS LSRGGRLSLSI |
| CXCR3LP2-1MI | 20 | ANIEKHDGGDDHKEINA |
| CXCL10-3-1MI | 21 | IEVHPSFGGFSPHVEI |
| CXCL10-3-2MI | 22 | IEVHPTFGGFTPHVEI |
| CXCL10-3-3MI | 23 | IEVHTFGGFTHVEI |
| CXCR3LP2-2MI | 24 | EKHDIGGDDHKEI |
| CR3-1 | 25 | DRFNSFRQPGGQRFSNFRD |
| CR3-2 | 26 | FVWQVAARVGGVRAAVQWVF |
| CR3-3 | 27 | DGVQPFNYQGGQYNFPQVGD |
| CRF-4 | 28 | NDALAGLRMLIRGGRIMRLGALADN |
| CRF-5 | 29 | LRMLIRGGRILMRL |
| CR3-1-1 | 30 | DRFNSYRQPGGQRYSNFRD |
| CR3-1-2 | 31 | DRYNSYRQPGGQRYSNYRD |
| CR3-2-1 | 32 | FVWQVFARVGGVRAFVQWVF |

TABLE 1-continued

| Name | SEQ ID NO: | Peptide Sequence |
|---|---|---|
| CR3-2-2 | 33 | FVWFARYGGYRAFWVF |
| CR3-3-1 | 34 | DGFQPFNYQGGQYNFPQFGD |
| CRF-4-1 | 35 | NDALFGLRMLIRGGRIMRLGFLADN |
| CRF-4-2 | 36 | NDWLFRMLIRGGRIMRFLWDN |
| CRF-4-3 | 37 | WLFRMWIRGGRWMRFLW |
| CRF-5-1 | 38 | LRFLIRGGRILFRL |
| CRF-5-2 | 39 | LRFLFRGGRFLFRL |
| CRF-5-3 | 40 | FRFLFRGGRFLFRF |
| CRF-5-4 | 41 | FRWLFRGGRFLWRF |
| CRF-5-5 | 42 | FRWLWRGGRWLWRF |

The protein-protein interactions of the various receptors with the peptides were conducted utilizing ClusPro (see Comeau et al., Nucl. Acids Res. 32: W96-99, W96-W99, DOI: 10.1093/nar/gkh354, 2004, incorporated herein by reference). This program is available on the internet at the Boston University website (nrc.bu.edu/cluster). The server preforms three computational steps: (1) rigid body docking by sampling conformation; (2) root-mean-square deviation (RMSD) based on clustering of the 1,000 lowest energy structures generated to find the largest clusters that will represent the most likely models of the complex, and (3) refinement of the selected structures using energy minimization. This in silico method is predictive of the interactions between test peptides and selected receptors. In the table below, "Dim Site BE" is the binding energy associated with the peptide's interaction with the site associated with dimerization of the receipt, and Lig Site BE" is the binding energy associate with the peptide's interaction with the site associated with ligand binding to the receptor.

TABLE 2

Data for protein-protein interactions*

| Blocking Peptide | Sequence | Dim Site BE | Lig Site BE |
|---|---|---|---|
| | First and Second Designs | Antagonist | Agonist |
| CXCL10-1 | VRSTSISGGSISTSRV (SEQ ID NO: 5) | -1,092.1 | |
| CXCL10-2 | IIPASQFGGFPQSAPII (SEQ ID NO: 6) | -1,339.8 | |
| CXCL10-3 | FSPRVEIGGIEVRPSF (SEQ ID NO: 7) | -1,479.6 | -1,485.3 |
| CXCL11-1 | FPMFKGGKFMPF (SEQ ID NO: 8) | -1,388.8 | |
| CXCL11-2 | RLSLSIGGISLSR (SEQ ID NO: 9) | -1,103.7 | -1,124.4 |
| CXCR3LP2-1 | DDHKEINAGGANIEKHD (SEQ ID NO: 10) | -1,148.0 | |
| CXCR3LP2-2 | DDHKEIGGIEKHD (SEQ ID NO: 11) | -872.7 | |
| CXCL10-3-1 | FSPHVEIGGIEVHPSF (SEQ ID NO: 12) | -1,492.2 | |
| CXCL10-3-2 | FTPHVEIGGIEVHPTF (SEQ ID NO: 13) | -1,506.9 | |
| CXCL10-3-3 | FTHVEIGGIEVHTF (SEQ ID NO: 14) | -1,463.5 | -1,377.6 |
| | Third Designs | | |
| CXCL10-1MI | SISTSRVGGVRSTSIS (SEQ ID NO: 15) | | -1,189.1 |
| CXCL10-2MI | FPQSAPIGGIIPASQF (SEQ ID NO: 16) | -1,353.4 | -1,168.6 |
| CXCL10-3MI | IEVRPSFGGFSPRVEI (SEQ ID NO: 17) | -1,361.4 | |
| CXCL11-1MI | KFMPFGGFPMFK (SEQ ID NO: 18) | -1,260.4 | |
| CXCL11-2MI | ISLSRGGRLSLSI (SEQ ID NO: 19) | -1,237.8 | |
| CXCR3LP2-1MI | ANIEKHDGGDDHKEINA (SEQ ID NO: 20) | -1,179.2 | |
| CXCL10-3-1MI | IEVHPSFGGFSPHVEI (SEQ ID NO: 21) | -1,452.4 | |
| CXCL10-3-2MI | IEVHPTFGGFTPHVEI (SEQ ID NO: 22) | -1,477.6 | |
| CXCL10-3-3MI | IEVHTFGGFTHVEI (SEQ ID NO: 23) | -1,364.4 | |
| CXCR3LP2-2MI | EKHDIGGDDHKEI (SEQ ID NO: 24) | -926.2 | |
| | Fourth Designs | Antagonist | Agonist |
| CR3-1 | DRFNSFRQPGGQRFSNFRD (SEQ ID NO: 25) | -1,485.1 | |
| CR3-2 | FVWQVAARVGGVRAAVQWVF (SEQ ID NO: 26) | | -1,775.5 |
| CR3-3 | DGVQPFNYQGGQYNFPQVGD (SEQ ID NO: 27) | -1,337.1 | -1,322.0 |
| CRF-4 | NDALAGLRMLIRGGRIMRLGALADN (SEQ ID NO: 28) | | -1,793.7 |
| CRF-5 | LRMLIRGGRILMRL (SEQ ID NO: 29) | | -1,533.1 |
| | Fifth Designs | | |
| CR3-1-1 | DRFNSYRQPGGQRYSNFRD (SEQ ID NO: 30) | -1,469.4 | |
| CR3-1-2 | DRYNSYRQPGGQRYSNYRD (SEQ ID NO: 31) | -1,407.0 | |
| CR3-2-1 | FVWQVFARVGGVRAFVQWVF (SEQ ID NO: 32) | | -1,807.7 |
| CR3-2-2 | FVWFARYGGYRAFWVF (SEQ ID NO: 33) | -1,928.1 | |
| CR3-3-1 | DGFQPFNYQGGQYNFPQFGD (SEQ ID NO: 34) | | -1,415.5 |
| CRF-4-1 | NDALFGLRMLIRGGRIMRLGFLADN (SEQ ID NO: 35) | | -1,852.0 |
| CRF-4-2 | NDWLFRMLIRGGRIMRFLWDN (SEQ ID NO: 36) | | -1,985.7 |
| CRF-4-3 | WLFRMWIRGGRWMRFLW (SEQ ID NO: 37) | | -1,948.6 |
| CRF-5-1 | LRFLIRGGRILFRL (SEQ ID NO: 38) | | -1,617.4 |
| CRF-5-2 | LRFLFRGGRFLFRL (SEQ ID NO: 39) | | -1,634.1 |
| CRF-5-3 | FRFLFRGGRFLFRF (SEQ ID NO: 40 | | -1,746.2 |

TABLE 2-continued

| Data for protein-protein interactions* | | | |
|---|---|---|---|
| Blocking Peptide | Sequence | Dim Site BE | Lig Site BE |
| CRF-5-4 | FRWLFRGGRFLWRF (SEQ ID NO: 41) | | -1,986.1 |
| CRF-5-5 | FRWLWRGGRWLWRF (SEQ ID NO: 42) | | -1,849.1 |

*CXCL10-Analogs; CXC11-Analogs; CR3-Blockers; CRF-More CXCL10 interactors

TABLE 3

| Name | SEQ ID NO: | Summary of Activities Peptide Sequence | |
|---|---|---|---|
| IP-10p | 1 | PESKAIKNLLKAVSKEMSKRSP | Agonist of CXCL10 |
| IP-10-1 | 2 | PESKVIKNLLKVASKERSKRSP | Agonist of CXCL10 |
| IP-10-2 | 3 | PESRVIKNLLRVVSKEKSRRSP | Agonist of CXCL10 |
| IP-10-3 | 4 | FAKAIKNFAKAVAKFA | Agonist of CXCL10 |
| CXCL10-1 | 5 | VRSTSISGGSISTSRV | Antagonist of CXCL10 |
| CXCL10-2 | 6 | IIPASQFGGFPQSAPII | Antagonist of CXCL10 |
| CXCL10-3 | 7 | FSPRVEIGGIEVRPSF | Both Antagonist and Agonist of CXCL10 |
| CXCL11-1 | 8 | FPMFKGGKFMPF | Antagonist of CXCL11 |
| CXCL11-2 | 9 | RLSLSIGGISLSR | Both Antagonist and Agonist of CXC11 |
| CXCR3LP2-1 | 10 | DDHKEINAGGANIEKHD | Antagonist of CXCR3 |
| CXCR3LP2-2 | 11 | DDHKEIGGIEKHD | Antagonist of CXCR3 |
| CXCL10-3-1 | 12 | FSPHVEIGGIEVHPSF | Antagonist of CXCL10 |
| CXCL10-3-2 | 13 | FTPHVEIGGIEVHPTF | Antagonist of CXCL10 |
| CXCL10-3-3 | 14 | FTHVEIGGIEVHTF | Both Antagonist and Agonist of CXCL10 |
| CXCL10-1MI | 15 | SISTSRVGGVRSTSIS | Antagonist of CXCL10 |
| CXCL10-2MI | 16 | FPQSAPIGGIIPASQF | Antagonist of CXCL10 |
| CXCL10-3MI | 17 | IEVRPSFGGFSPRVEI | Both Antagonist and Agonist of CXCL10 |
| CXCL11-1MI | 18 | KFMPFGGFPMFK | Antagonist of CXCL11 |
| CXCL11-2MI | 19 | ISLSRGGRLSLSI | Both Antagonist and Agonist of CXCL11 |
| CXCR3LP2-1MI | 20 | ANIEKHDGGDDHKEINA | Antagonist of CXCR3 |
| CXCL10-3-1MI | 21 | IEVHPSFGGFSPHVEI | Antagonist of CXCL10 |
| CXCL10-3-2MI | 22 | IEVHPTFGGFTPHVEI | Antagonist of CXCL10 |
| CXCL10-3-3MI | 23 | IEVHTFGGFTHVEI | Antagonist of CXCL10 |
| CXCR3LP2-2MI | 24 | EKHDIGGDDHKEI | Antagonist of CXCR3 |

TABLE 3-continued

Summary of Activities

| Name | SEQ ID NO: | Peptide Sequence | |
|---|---|---|---|
| CR3-1 | 25 | DRFNSFRQPGGQRFSNFRD | Antagonist of CXCR4? |
| CR3-2 | 26 | FVWQVAARVGGVRAAVQWVF | Agonist of CXCR4 |
| CR3-3 | 27 | DGVQPFNYQGGQYNFPQVGD | Both Antagonist and Agonist of CXCR4 |
| CRF-4 | 28 | NDALAGLRMLIRGGRIMRLGALADN | Antagonist of CXCL10 |
| CRF-5 | 29 | LRMLIRGGRILMRL | Antagonist of CXCL10 |
| CR3-1-1 | 30 | DRFNSYRQPGGQRYSNFRD | Antagonist of CXCR4 |
| CR3-1-2 | 31 | DRYNSYRQPGGQRYSNYRD | Antagonist of CXCR4 |
| CR3-2-1 | 32 | FVWQVFARVGGVRAFVQWVF | Agonist of CXCR4 |
| CR3-2-2 | 33 | FVWFARYGGYRAFWVF | Antagonist of CXCR4 |
| CR3-3-1 | 34 | DGFQPFNYQGGQYNFPQFGD | Agonist of CXCR4 |
| CRF-4-1 | 35 | NDALFGLRMLIRGGRIMRLGFLADN | Agonist of CXCL10 |
| CRF-4-2 | 36 | NDWLFRMLIRGGRIMRFLWDN | Agonist of CXCL10 |
| CRF-4-3 | 37 | WLFRMWIRGGRWMRFLW | Agonist of CXCL10 |
| CRF-5-1 | 38 | LRFLIRGGRILFRL | Agonist of CXCL10 |
| CRF-5-2 | 39 | LRFLFRGGRFLFRL | Agonist of CXCL10 |
| CRF-5-3 | 40 | FRFLFRGGRFLFRF | Agonist of CXCL10 |
| CRF-5-4 | 41 | FRWLFRGGRFLWRF | Agonist of CXCL10 |
| CRF-5-5 | 42 | FRWLWRGGRWLWRF | Agonist of CXCL10 |

Example 2: Materials and Methods

This example describes the experimental procedures for the studies described in Example 3.

Animals

Wild-type FVB mice were obtained from the Jackson Laboratory. CXCR3−/− mice were bred from male and female CXCR3−/− mice and genotyped prior to their use.

IP-10p Peptide Synthesis

IP-10p (SEQ ID NO: 1) was synthesized as previously described (Yates-Binder et al., *PLoS ONE* 7(7):e40812, 2012). Briefly, fMOC chemistry was used to synthesize the 22 amino acid peptide and purified with HPLC. The sequence, purity, and relative mass were confirmed prior to its use. Additionally, the TFA was neutralized in cell culture media prior to all experiments.

Primary Cardiac Cell Isolation and Culture

Primary cardiac fibroblasts and cardiomyocytes were isolated from both wild-type and CXCR3−/− neonatal mouse pups. After washing in PBS, hearts were stirred for 5 minutes in 0.5% trypsin at 37° C. to dissociate cells into solution. The suspended cells were then transferred to DMEM containing 20% fetal bovine serum (FBS) on ice to inactivate trypsin activity, and dissociation was repeated twice more with fresh trypsin solution. Cells were then washed and plated into 6-well plates at $1.25 \times 10^6$ cells/well, suspended in cardiac cell media (DMEM containing 7.5% dialyzed FBS and 1% antibiotic/antimitotic solution). After three hours, adhered fibroblasts were separated from the unattached cardiomyocytes through resuspension of the cells, and cardiomyocytes were plated separately at a density of $5 \times 10^5$ cells/ml.

To confirm successful isolation of fibroblasts and cardiomyocytes, a sample of each cell type were stained for vimentin, a fibroblast marker. After fixing in ice cold methanol for 10 minutes and permeabilization in 0.5% triton X-100, cells were stained with an anti-vimentin antibody (1:50, Abcam ab92547, Cambridge, UK) overnight at 4° C. followed by a secondary Alexa Fluor 488 (1:250, Abcam ab150077)-conjugated antibody. Cells were counterstained with 4,6-diamidino-2-phenylindole (DAPI) (Vector Laboratories, Burlingame, Calif.). The fraction of isolated cells expressing vimentin was calculated for isolated fibroblasts (positive marker) and cardiomyocytes (negative marker).

Motility Assay

To determine the effect of IP-10p on TGFβ1-induced cell migration, motility assays were performed on cardiac fibroblasts, cardiomyocytes, and co-cultures (2:1 ratio of cardiomyocytes to fibroblasts). Cells were plated at $2.5 \times 10^5$ cells/well in a 12-well uncoated plate in depleted media (DMEM containing 0.5% FBS) 24 hours before beginning the experiment. A pipette tip was used to create a scratch in the monolayer and the plate was washed twice with PBS to remove scraped cells. Cells were then treated with TGFβ1 (R&D Systems, Minneapolis, Minn.) alone (10 ng/mL) to stimulate fibrosis, CXCL10 alone (10 μM), IP-10p alone (10 μM), TGFβ1+CXCL10, TGFβ1+IP-10p, or left untreated. Images were taken immediately after scratching and 24 hours later, and Adobe Photoshop was used to quantify wound motility as distance between wound edges relative to the initial scratch width.

Fibroblast Activation Assay

Fibroblast activation to myofibroblasts is marked by aSMA expression within the cytoskeleton and serves as a marker to induce fibrosis. Cardiac fibroblasts were plated at 2,000 cells/well in an 8-well chamber slide and allowed to adhere overnight. After 24 hours, cells were washed and treated with: TGFβ1 alone (10 ng/ml), CXCL10 alone (10 μM), IP-10p alone (10 μM), TGFβ1+CXCL10, TGFβ1+IP-10p, or left untreated. After 24 hours, cells were fixed in ice cold methanol for 10 minutes and stained for aSMA (1:200, Abcam ab5694, Cambridge, UK) at 4° C. overnight, followed by a goat-anti-rabbit Alexa Fluor 594-conjugated secondary antibody (Abcam ab150080). After counterstaining with DAPI, cells were imaged, and fibroblast activation was measured using corrected total cell fluorescence (CTCF). These measurements were also performed in co-cultures of cardiomyocytes and cardiac fibroblasts (2:1 ratio)

Fibrotic Extracellular Matrix (ECM) Secretion

Cardiac fibrosis is marked by overproduction of ECM proteins following injury. To observe the effect of IP-10p on secretion of these molecules, co-cultures of cardiomyocytes and cardiac fibroblasts were used to account for intracellular signaling taking place between the two dominant cell types in the heart. Fibroblasts and myocytes were plated at a 2:1 ratio using the same culture conditions and treatment groups described above for fibroblast activation. Following a 48-hour incubation with their respective treatments, cells were fixed, permeabilized and stained. Antibodies for collagen α1 type 1 (1:250, Santa Cruz Biotechnology SC8784, Dallas, Tex.), fibronectin (1:250, Abcam ab2413), and tenascin C (1:200, Abcam ab6346), followed by their appropriate secondary antibodies (Abcam ab150132, ab150077, and 150153, respectively), were used to determine fibrotic ECM secretion from the co-cultures. Expression of these molecules is expressed at CTCF and was quantified using MetaMorph® (Molecular Devices, Sunnyvale, Calif.).

Western Immunoblot

Fibroblasts, cardiomyocytes, and co-cultures were plated and treated as described above and were treated with one of the same treatments. Twenty-four hours later, cells were detached from the plate with trypsin, washed, and lysed in NP40 lysis buffer containing proteasome inhibitors. A 10 μl lysate was prepared and the proteins separated using SDS-PAGE followed by transfer to a nitrocellulose membrane. Membranes were probed for: p-SMAD2/3 (1:1000, Cell Signaling Technology 8288S, Danvers, Mass.), total SMAD2/3 (1:1000), p-ERK (1:1000, Cell Signaling Technology 9101S), total ERK (1:1000), phospho-p38 (1:1000), or total p38 (1:1000, Cell Signaling Technology 9212S).

Statistics

All quantitative assays were performed at least three times in triplicate. Results are expressed as mean±SEM.

Example 3: IP-10-Derived Peptide Inhibits TGFβ1-Induced Cardiac Fibrosis

This example demonstrates that cardiac fibroblasts treated with IP-10 peptide (IP-10p; SEQ ID NO: 1) reduce expression of α-smooth muscle actin along with secretion of collagen and fibronectins. In addition, IP-10p inhibits TGFβ1-induced cell migration with the same efficacy as the whole protein in multiple cardiac cell types. Further, IP-10p is able to signal in a pathway independent of its only known receptor CXCR3. These results indicate the importance of the α-helical domain in preventing TGFβ1-induced cardiac fibrosis and shows the potential of IP-10p as a therapeutic to prevent fibrosis following MI.

CXCL10 and IP-10p Inhibit Cardiac Cell Motility

Cardiac cell motility in response to IP-10p and CXCL10 was determined independently and in combination with pro-fibrotic TGFβ1. Compared to control, motility of cardiac fibroblasts was not altered when treated with CXCL10 or the mimicking peptide IP-10p alone. However, the addition of TGFβ1 increased motility over 3-fold relative to untreated cells. The addition of CXCL10 to fibroblasts treated with TGFβ1 reduced motility by 30%. IP-10p reduced motility of TGFβ1-treated fibroblasts by over 40%, more than the intact CXCL10 protein. Similar trends were seen in cardiomyocytes and co-cultures of cardiomyocytes and cardiac fibroblasts. CXCL10 and IP-10p completely inhibited cardiomyocyte motility in the presence of TGFβ1. This indicates successful inhibition of TGFβ1-induced cell migration in response to the CXCL10-mimicking IP-10p.

IP-10p Inhibits TGFβ1-Induced Myofibroblast Activation

Fibroblast activation by TGFβ1 plays a role in fibrosis through upregulation of ECM proteins. To determine the effect of the CXCL10-mimicking peptide IP-10p, cardiac fibroblasts were stimulated with TGFβ1 and treated with IP-10p. Treatment with TGFβ1 drastically increased aSMA expression, signifying activation of the fibroblasts compared to the untreated control. IP-10p alone reduced activation of fibroblasts by 33% compared to the untreated control; further, IP-10p also reduced aSMA expression in the presence of TGFβ1 compared to cells activated with TGFβ1 alone. Similar results were obtained for this experiment when performed on co-cultures of cardiomyocytes and cardiac fibroblasts. This indicates IP-10p inhibits fibroblast activation, even in the presence of TGFβ1.

Fibroblast activation also results in overexpression of secreted collagen and fibronectin that leads to fibrosis. Co-cultures of cardiac fibroblasts and cardiomyocytes treated with TGFβ1 showed significant upregulation of both collagen and fibronectin relative to unstimulated cultures. However, IP-10p reduced expression of both these proteins to baseline levels in the presence of TGFβ1, showing successful inhibition of fibrotic protein secretion. Co-cultures treated with IP-10p alone in the absence of TGFβ1 also showed reduced collagen and fibronectin secretion compared to unstimulated cultures. Similar trends in aSMA, collagen, and fibronectin expression were seen between cultures treated with CXCL10 and cultures treated with IP-10p, indicating the IP-10p peptide behaves similarly to the whole protein when exposed to TGFβ1.

Cardiac Cell Motility is Independent of CXCR3-Mediated Signaling in Response to IP-10p CXCR3 is the single identified receptor of CXCL10, although recent evidence suggests that CXCL10 can signal through an alternative CXCR3-independent pathway that has not yet been fully identified. As IP-10p is an α-helical peptide derived from CXCL10, the effects of IP-10p on CXCR3−/− cells were tested to determine if the peptide also possesses an alternative signaling pathway. Co-cultures of cardiac fibroblasts and cardiomyocytes from CXCR3−/−rats were stimulated with TGFβ1 in the presence or absence of IP-10p to determine its effect on cell motility.

IP-10p Modulates Myofibroblast Differentiation Independent of CXCR3

In addition to cell motility, myofibroblast differentiation in CXCR3−/− cells in response to IP-10p was assessed. Similar to wild-type cells, IP-10p inhibited upregulation of collagen I and fibronectin while inhibiting expression of aSMA in co-cultures of cardiac fibroblasts and cardiomyocytes. This behavior is similar to that seen in cultures treated with whole CXCL10 in the presence of TGFβ1. Taken together, this data suggests that CXCR3 is not the signaling mechanism regulating CXCL10 and IP-10p-mediated inhibition of collagen and fibronectin secretion. Additionally, it indicates that the α-helical portion of CXCL10 is at least partially responsible for CXCR3-independent signaling seen in the cardiac environment.

IP-10p Modulates Signaling in Wild-Type Cardiac Cells

To elucidate some of the signaling mechanisms responsible for these changes in cell behavior and expression, cardiac fibroblasts, cardiomyocytes and co-cultures were stimulated with TGFβ1 in the presence or absence of IP-10p.

Therapeutic Applications

The study disclosed herein demonstrates the ability of a CXCL10-mimicking peptide, IP-10p, to inhibit TGFβ1-induced motility, myofibroblast differentiation, and subsequent secretion of fibrotic extracellular proteins such as collagen I. IP-10p is a 22-amino acid CXCL10 agonist that spans the C-terminal residues (77-98) of IP-10, encompassing the alpha-helical region. This peptide competes for binding and activation of CXCR3 in an equimolar manner to whole CXCL10. The present disclosure shows that IP-10p is able to inhibit growth factor-induced migration in cardiac fibroblasts and cardiomyocytes. While this activity was attributed to the CXCR3 signaling pathway in endothelial cells, the present data suggests that CXCL10 is able to act outside of this sole known receptor in the heart. This study shows that while IP-10p successfully inhibits TGFβ1-induced fibrosis in vitro, this action cannot be attributed solely to binding and activation of CXCR3. Cells from CXCR3−/− mice showed similar inhibition of motility and reduced myofibroblast differentiation to cells from wild-type mice, indicating an alternative pathway is present. Additionally, since IP-10p is derived from the α-helical portion of the CXCL10 protein, these results suggest that this region of CXCL10 is at least partially responsible for the CXCR3-independent signaling seen in the heart.

Cardiac fibrosis is characterized by excessive secretion of a fibrous ECM starting at the infarct region and expanding throughout the ventricle over time. These ECM proteins are first secreted as a protective mechanism to prevent rupture of the ventricle wall and maintain heart function. Unlike other tissues, these proteins are continuously produced even after the initial inflammatory phase, leading to a buildup of a stiff collagen scar that expands into otherwise healthy cardiac tissue, ultimately stiffening the ventricle wall. TGFβ1 through SMAD signaling is one accepted route of profibrotic ECM secretion in cardiac fibroblasts. The present study shows that the use of IP-10p on TGFβ1-treated fibroblasts is able to reduce secretion of fibrotic matrix proteins collagen I and fibronectin, indicating its potential as an anti-fibrotic therapy.

Another approach to preventing cardiac fibrosis is preventing myofibroblasts from entering the infarct region. Due to the widespread presence of cardiac fibroblasts in the heart, they often serve as first responders after injury, differentiating into myofibroblasts to recruit inflammatory cells and secrete extracellular proteins. This migration and differentiation is regulated at least partially by high levels of TGFβ1, which was simulated in the in vitro experiments described herein. Prevention of fibroblast migration and differentiation in response to TGFβ1 should therefore ultimately mitigate fibrosis following MI. The use of IP-10p, similar to CXCL10, successfully inhibits migration of cardiac fibroblasts, exhibiting its ability to prevent a mass migration of profibrotic fibroblasts to the injury site in the acute stage of MI. Further, IP-10p also prevents differentiation of fibroblasts into myofibroblasts. Therefore the use of IP-10p has at least 3 identified mechanisms of action to prevent fibrosis: inhibiting migration of fibroblasts to the infarct region, preventing differentiation into proinflammatory myofibroblasts, and preventing excessive secretion of stiff collagen and fibronectin proteins.

There is broad interest in developing anti-fibrotic drugs whose primary application is related to lung, liver, kidney, and skin diseases. Many drugs to treat these diseases are in clinical trials. However, despite the link between cardiac fibrosis and heart failure, therapies targeting cardiac fibrosis in heart failure and/or after a heart attack do not yet exist. Several anti-fibrotic candidates have been tested in rodent myocardial infarction models, including Tolvaptan (a non-peptide V2-receptor antagonist), G-CSF, endostatin, MAPKAP Kinase 2 inhibition, and p38 inhibitor. Simvastatin, a drug in the statin class of anti-cholesterol drugs, has recently been shown to reduce cardiac fibrosis post-MI in rodent models by regulating TGFβ receptor III expression. While promising, all these therapies have limited if any experimental data presented in humans. Tolvaptan is being investigated in heart failure in several clinical trials, but cardiac fibrosis has yet to be named as a primary outcome measurement. Currently, Simvastatin and Rosuvastatin are being investigated in phase 4 trials with platelet inhibitors in coronary artery disease investigating its effects on myocardial fibrosis, but results from the study have not yet been posted.

This study evaluated the potential of a CXCL10 peptide mimic to mitigate TGFβ1-induced cardiac fibrosis in vivo. The results indicate that IP-10p is able to signal outside of CXCR3 in the cardiac environment similarly to whole CXCL10, which has not been shown previously. The connection of fibrosis to heart failure and cardiac dysfunction emphasizes the importance of novel anti-fibrotic therapies such as IP-10p for clinical translation.

Example 4: Small Peptide Antagonists Block CXCL10-CXCR3 Signaling and Function on Cardiac Fibroblasts and Cardiomyocytes Myocarditis is an inflammatory disease of the heart muscle that often results in cardiac dysfunction and death, especially in young patients. One of the causes of myocarditis is viral infection. The severe cardiac inflammation that characterizes the pathogenesis of myocarditis is mediated by leukocytes entering the cardiac tissue, and is often accompanied by remodeling and cardiomyocyte apoptosis. Possible cell sources for viral replication are cardiac fibroblasts (CF) and cardiomyocytes (CM), thought to be important contributors of virus replication, which aggravate myocarditis. It has been observed that CXCL10 is unregulated in the myocardium during the early stages of infection. CXCL10 is thought to be the master regulator of myocardial interactions between cardiac and immune cell migration, potentially affecting cardiac damage and the clinical progression of myocarditis. It has been previously shown that CXCL10, via its receptor CXCR3, inhibits growth factor-induced motility in both CF and CM. Currently, clinical therapies for myocarditis are predominantly based on symptoms and diagnosis of the underlying infection, but lack a targeted approach to inhibiting the cardiac damage induced by infections. To address this need, peptides with the potential to inhibit the cardiac damage induced by infections were designed, developed, and tested in vitro.

This example describes the testing of two small (14 amino acid) peptide antagonists of CXCL10-CXCR3, referred to as CRF-5-3 (SEQ ID NO: 40) and CRF-5-5 (SEQ ID NO: 42), which were developed by in silico prediction-based functional peptide design to directly bind to CXCL10 (see Example 1).

CM and CF were isolated from wild type and CXCR3-null FVB neonatal mice. Following isolation, CM, CF, or CM/CF in both direct and indirect co-cultures were challenged with CM and CF activating growth factor transforming growth factor β (TGF-β). Antagonist peptide treatments, CRF-5-3 and CRF-5-5, were given alone or in combination with CXCL10. To determine whether CRF-5-3 and CRF-5-5 block CXCL10 binding to its receptor, the ability of biotin-tagged CXCL10 and/or FITC-tagged CRF-5-5 to compete for binding to CM and CF was analyzed using flow cytometry. In vitro cellular function assays were assessed for migration, apoptosis, and extracellular matrix (ECM) secretion. Real time quantitative polymerase chain reaction was employed in order to determine modified relative gene expression of both CM and FB, following treatment.

The results demonstrated that CRF-5-3 and CRF-5-5 altered CXCL10-induced gene expression on both FB and CM. CRF-5-5 interfered with CXCL10 inhibition of TGF-β-induced matrix production. Meanwhile, CRF-5-3 and CRF-5-5 altered CXCL10 inhibition of TGF-β-induced P38 mitogen-activated protein kinase (MAPK)-dependent extracellular matrix production in cardiac fibroblasts. Histochemical and fluorescence analyses of CM/CF co-cultures revealed ECM CRF-5-3-mediated alterations following TGF-β and/or CXCL10 treatment.

These data demonstrate that CRF-5-3 and CRF-5-5 promote the disinhibition of CXCL10-suppressed growth factor-induced intracellular P38 signaling, motility, and ECM production.

Example 5: Treatment of Primary Lung Fibroblasts with IP-10-Related Peptides

This example describes the effects of IP-10 related peptides (SEQ ID NOs: 2-4) on lung fibroblast viability, pro-fibrotic mRNA expression and TGF-β-induced cell migration.

The effect of IP-10-related peptides on viability of lung fibroblasts was evaluated. Primary lung fibroblasts from healthy patients (SC31 and SC45) were either left untreated or treated with various concentrations of peptides (1 to 1000 ng/mL) for 24 hours. Treatment for 30 minutes with 70% ethanol in water was used as a positive control for dead cells. The Molecular Probes LIVE/DEAD Viability/Cytotoxicity Kit for mammalian cells (Invitrogen) was used to stain live cells. Following the manufacturer's protocol, at the end of treatment, cells in 96-well plates were washed with PBS, and then incubated in 2 μM Calcein-AM solution for 45 minutes at room temperature. Following incubation, the cells were imaged under a fluorescence microscope using the GFP channel. For quantification, ImageJ was used to count the number of live cells per field.

Figure 2A:
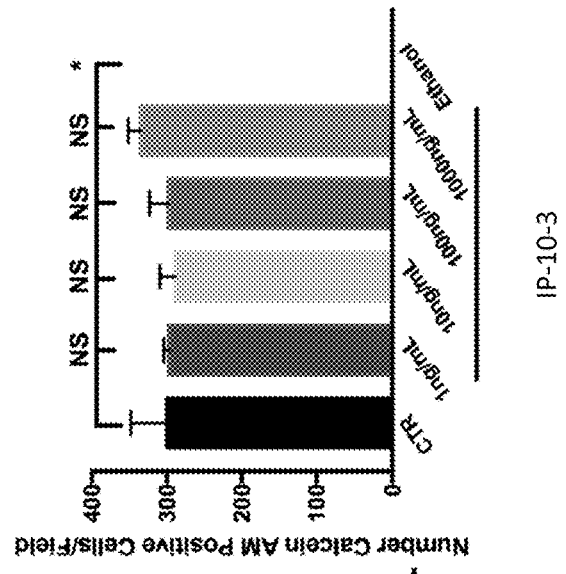
FIGS. 2A-2C: Fibroblast viability activity is unaffected by IP-10-related peptides. Treatment with various concentrations of IP-10-1 (FIG. 2A), IP-10-2 (FIG. 2B), or IP-10-3 (FIG. 2C) ranging from 1 ng/mL to 1000 ng/mL for 24 hours had no impact on the number of viable cells as measured by ability to take up Calcein-AM dye. Mean+/−SEM are shown in the graph.
Figure 2B:
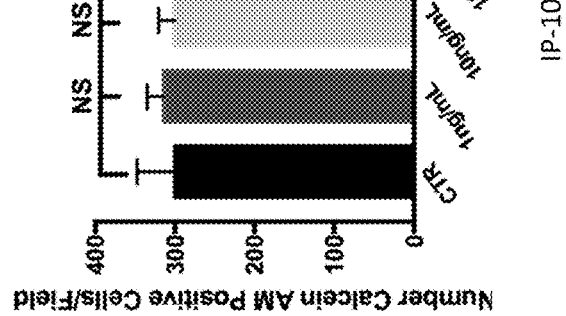
Figure 2C:
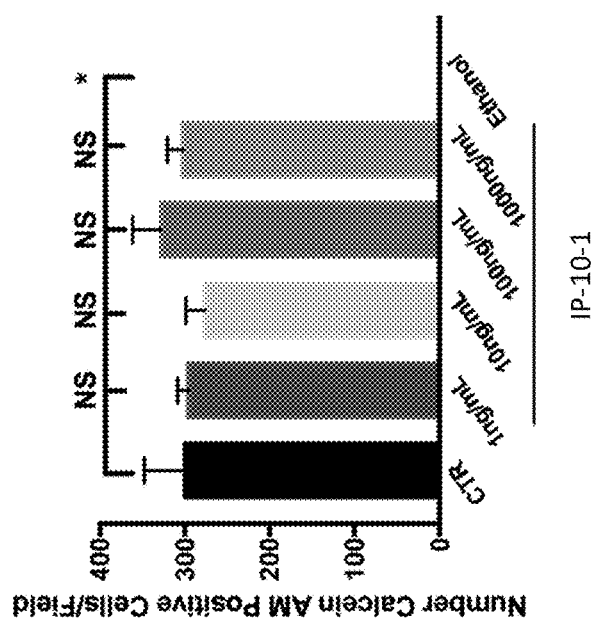

The quantity of live cells (as measured by uptake of Calcein-AM dye) after treatment with the IP-10 related peptides is shown in FIG. 2A (IP-10-1; SEQ ID NO: 2), FIG. 2B (IP-10-2; SEQ ID NO: 3) and FIG. 2C (IP-10-3; SEQ ID NO: 4). At the concentrations tested (1-1000 ng/mL), none of the peptides had any significant effect on cell viability after 24 hours of treatment. Treatment with ethanol resulted in elimination of the detected Calcein-AM positive cells, indicating that the assay was sensitive to cell death. This result demonstrates that the peptides do not elicit fibroblast toxicity within the 24 hour treatment time period.

To further evaluate the IP-10-related peptides, studies were conducted to determine whether treatment of primary lung fibroblasts with the peptides could alter the expression of pro-fibrotic mRNAs.

Primary lung fibroblasts from healthy patients (SC31 and SC45) were plated in 6-well plates in complete medium and incubated overnight. The next day, the medium was changed to quiescent medium and the cells were incubated in this medium for 24 hours. The following day, cells were either left untreated, treated with 10 ng/mL or 100 ng/mL of IP-10-1 (SEQ ID NO: 2), IP-10-2 (SEQ ID NO: 3) or IP-10-3 (SEQ ID NO: 4) peptide, treated with 10 ng/mL TGF-β, or treated with peptide and TGF-β for 24 hours. Total RNA was extracted using the Qiagen miRNeasy kit (Qiagen) and treated with DNase1, according to the manufacturer's instructions. RNA was then quantified and converted to cDNA using the Clontech RNA to cDNA EcoDry Double Primed Premix (Takara). qPCR was performed using PowerUp Sybr Green (Invitrogen) on an Applied Biosystems Quant Studio 3 instrument. Primers were from IDT and were designed using IDT Primer Quest and NCBI Primer Blast tools. The delta-delta Ct method was used to determine relative expression. GAPDH was used as a housekeeping gene.

Figures 3A, 3B, 3C, 3D, 3E:
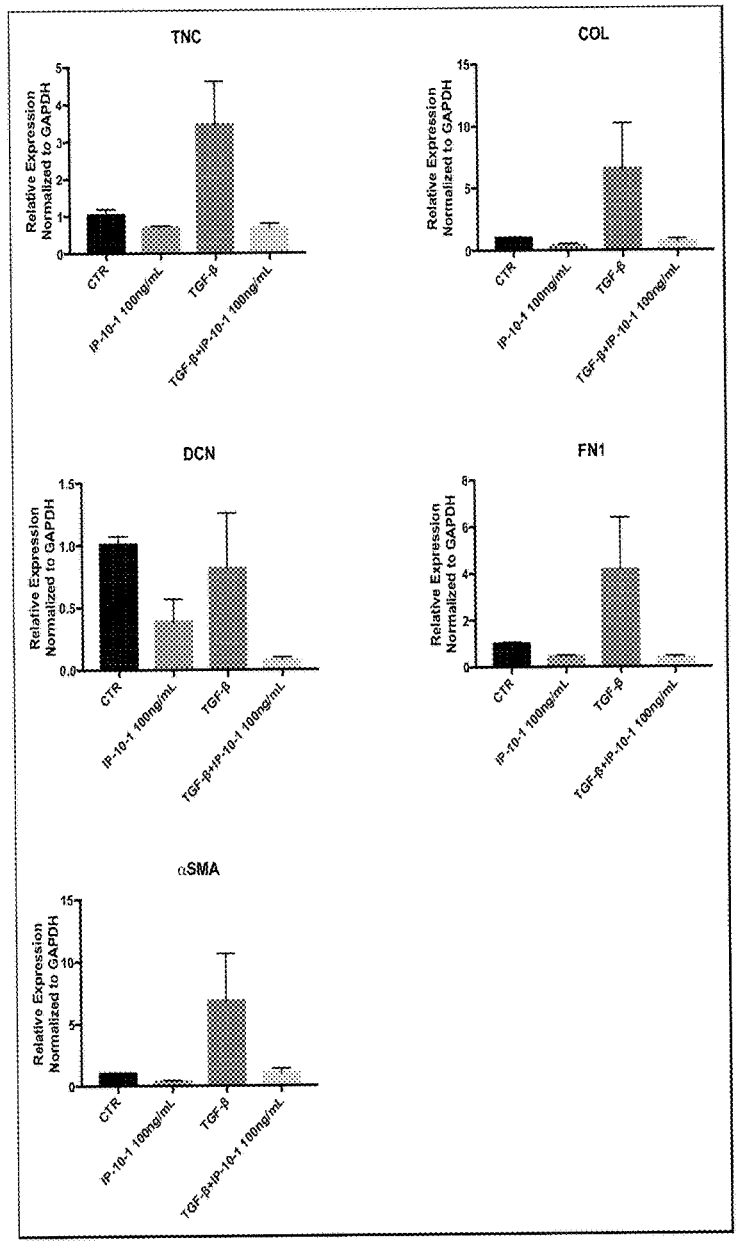
FIGS. 3A-3O: IP-10-1 and IP-10-2 peptides inhibit TGF-$\beta$-mediated induction in expression of pro-fibrotic mRNAs. Treatment with IP-10-1 alone (100 ng/mL) had no effect on mRNA expression of tenascin C (TNC.
FIG. 3B), fibronectin 1 (FN1.
FIG. 3D), or alpha smooth muscle actin (aSMA.
FIG. 3E), but reduced the level of decorin (DCN.
FIG. 3C). Treatment with IP-10-2 alone (100 ng/mL) increased expression of TNC (FIG. 3F), COL1A1 (FIG. 3G), DCN (FIG. 3H), FN1 (FIG. 3I), and aSMA (FIG. 3J). Treatment with IP-10-3 alone (100 ng/mL) had no effect on expression of TNC (FIG. 3K), COL1A1 (FIG. 3L), DCN (FIG. 3M), FN1 (FIG. 3N), or aSMA (FIG. 3O). Treatment with TGF-$\beta$ (10 ng/mL) induced expression of mRNAs for TNC (FIGS. 3A, 3F, 3K), COL1A1 (FIGS. 3B, 3G, 3L), FN1 (FIGS. 3D, 3I, 3N), and aSMA (FIGS. 3E, 3J, V3O) in primary lung fibroblasts. When added with TGF-$\beta$, IP-10-1 reduced the induction in mRNA expression of TNC (FIG. 3A), COL1A1 (FIG. 3B), FN1 (FIG. 3D), and aSMA (FIG. 3E) and reduced levels of DCN (FIG. 3C). When IP-10-2 was added along with TGF-$\beta$, it prevented induction in TNC (FIG. 3F), COL1A1 (FIG. 3G), FN1 (FIG. 3I), and aSMA (FIG. 3J). When IP-10-3 was added with TGF-$\beta$, the peptide slightly decreased expression of TNC (FIG. 3K), COL1A1 (FIG. 3L), and aSMA (FIG. 3O) compared to TGF-$\beta$ treatment.
Figures 3F, 3G, 3H, 3I, 3J:
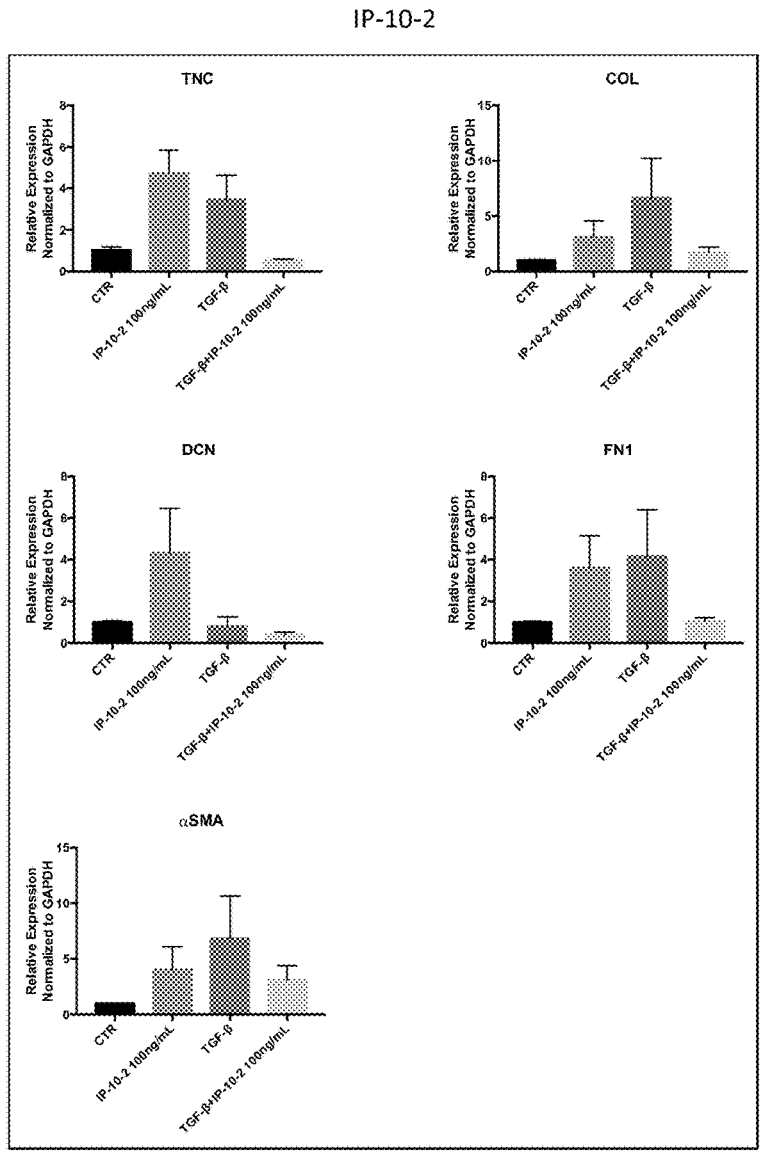
Figures 3K, 3L, 3M, 3N, 3O:
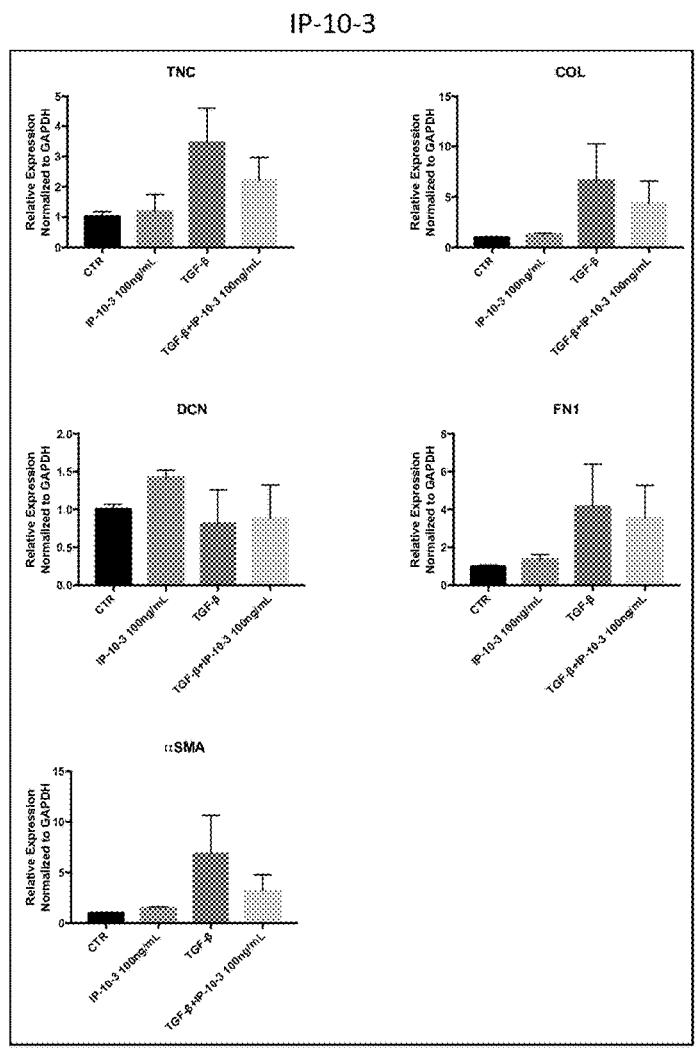

The results of the 100 ng/mL experiment (FIGS. 3A-3O) demonstrated that IP-10-1 and IP-10-2 potently inhibited the effects of TGF-β on expression of TNC, COL1A1, FN1, and aSMA. IP-10-3 had a lesser effect but inhibited the TGF-β-mediated increase in aSMA. The effects on DCN were less straightforward: IP-10-1 alone decreased expression of DCN, while IP-10-2 enhanced its expression. In the presence of TGF-β, both IP-10-1 and IP-10-2 decreased expression of DCN compared to no treatment.

Figures 4A, 4B, 4C, 4D, 4E:
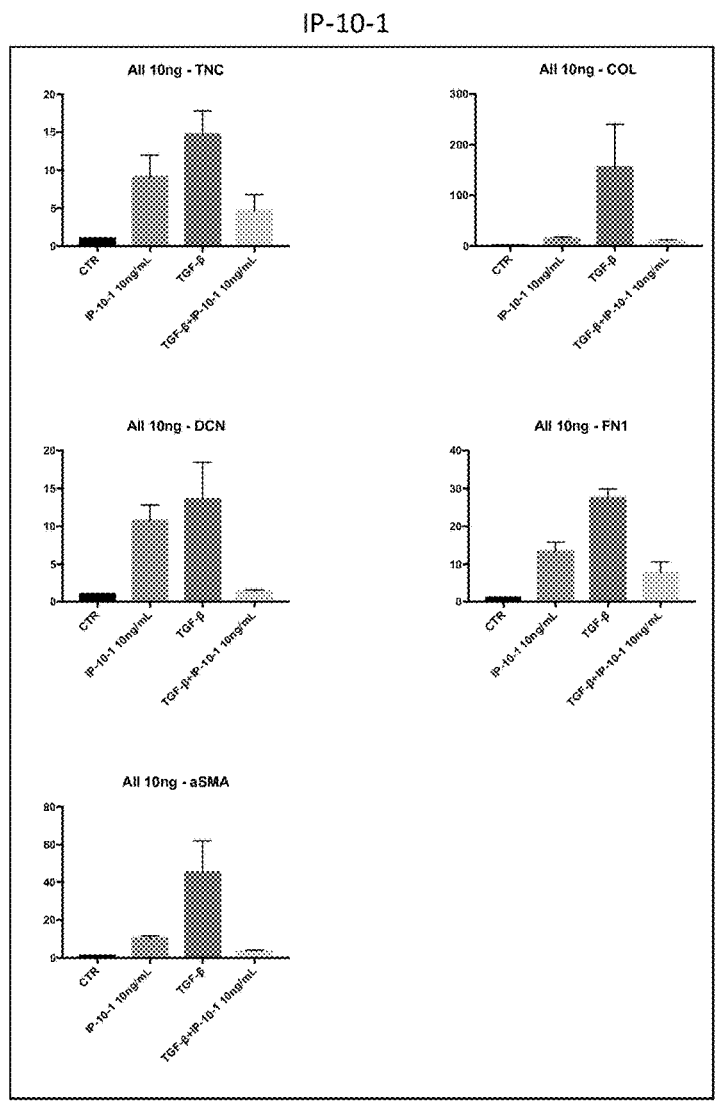
FIGS. 4A-4O: IP-10-related peptides inhibit TGF-$\beta$-mediated induction in expression of pro-fibrotic mRNAs. When treated with IP-10-1 (10 ng/mL) alone, primary lung fibroblasts induced mRNA expression of TNC (FIG. 4A), COL1A1 (FIG. 4B), DCN (FIG. 4C), FN1 (FIG. 4D), and aSMA (FIG. 4E). Treatment with IP-10-2 alone (10 ng/mL) resulted in little changes in gene expression. Treatment with IP-10-3 (10 ng/mL) alone caused an induction in expression of TNC (FIG. 4K), DCN (FIG. 4M), FN1 (FIG. 4N), and aSMA (FIG. 4O). As expected, treatment with TGF-$\beta$ (10 ng/mL) caused an induction in the levels of TNC (FIGS. 4A, 4F, 4K), COL1A1 (FIGS. 4B, 4G, 4L), FN1 (FIGS. 4D, 4I, 4N), and aSMA (FIGS. 4E, 4J, 4O). An induction in DCN was also observed (FIGS. 4C, 4H, 4M). When IP-10-1 was added along with TGF-$\beta$, there was a significant reduction in expression of TNC (FIG. 4A), COL1A1 (FIG. 4B), DCN (FIG. 4C), FN1 (FIG. 4D), and aSMA (FIG. 4E) compared to treatment with TGF-$\beta$ only. Similarly, treatment with IP-10-2 or IP-10-3 along with TGF-β substantially reduced the induction by treatment with TGF-b alone
Figures 4F, 4G, 4H, 4I, 4J:
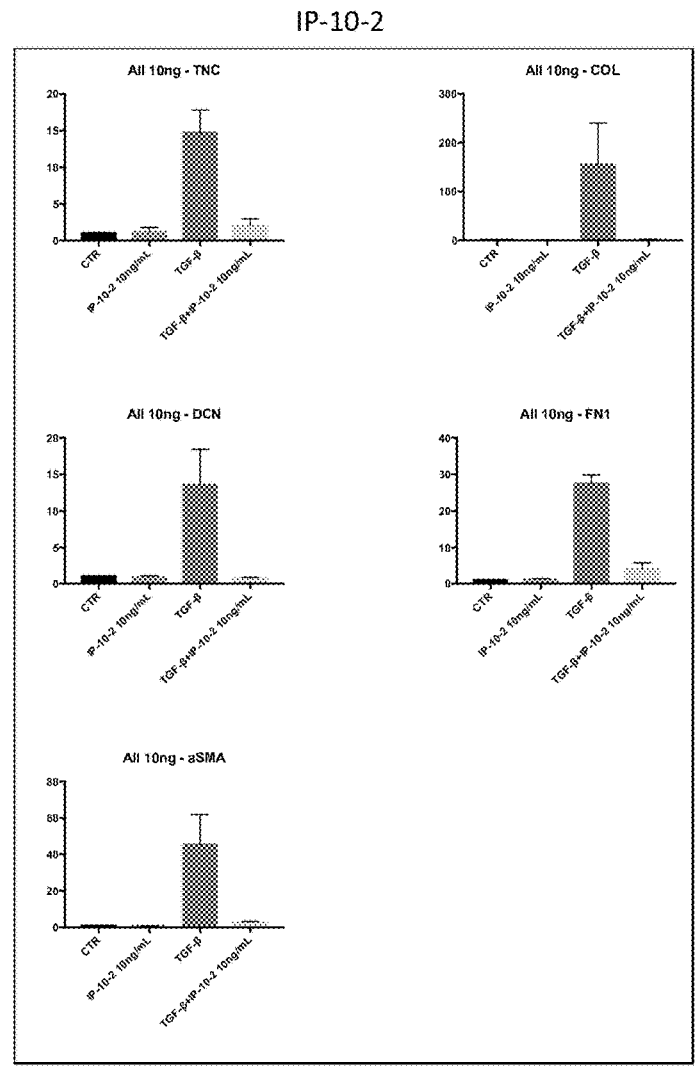
Figures 4K, 4L, 4M, 4N, 4O:
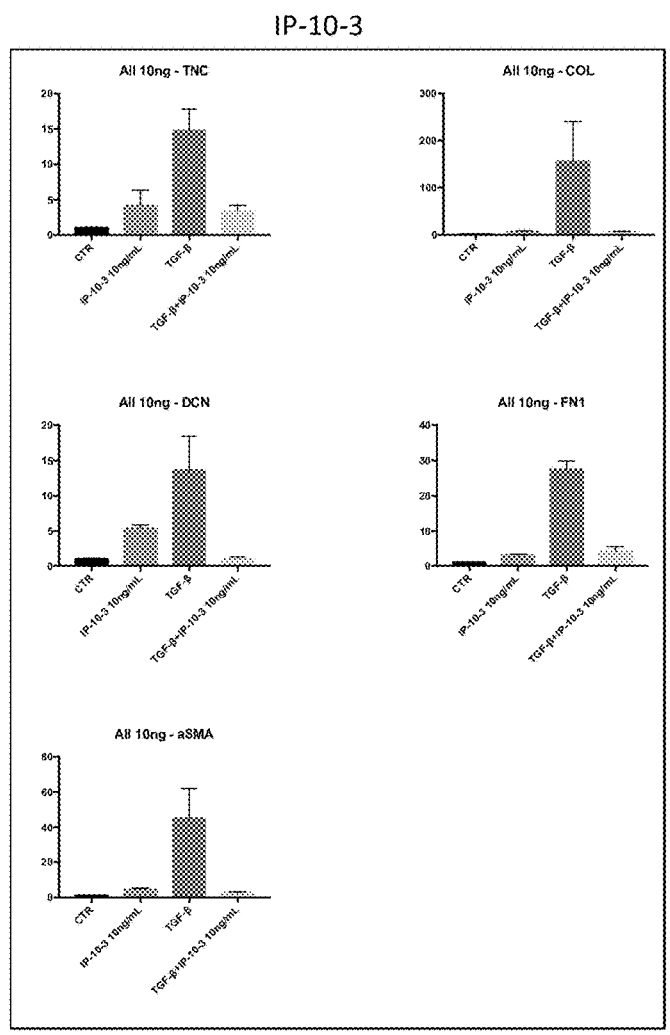

For the 10 ng/mL peptide experiments (FIGS. 4A-4O), treatment with TGF-β for 24 hours induced expression of mRNAs for TNC, COL1A1, DCN, FN1, and aSMA. When cells were treated with 10 ng/mL IP-10-1, IP-10-2, or IP-10-3 along with TGF-β (fourth bars of each graph), this induction was dramatically inhibited. Treatment with IP-10-1 alone increased expression of TNC, DCN, FN1, and aSMA to some extent. Similarly, IP-10-3 alone induced expression of TNC and DCN a small amount.

Next, studies were performed to evaluate the effect of IP-10 related peptides on migration of lung fibroblasts in response to TGF-β. Primary lung fibroblasts from healthy patients were plated in 24-well plates in complete medium and incubated overnight. The next day, the medium was changed to quiescent medium and cells were incubated in this medium for 24 hours. The following day, a plus-shaped scratch was made across the cells using a 1000 μL pipette tip. An image was taken at a location that could be identified later. After imaging, cells were either left untreated, treated with 100 ng/mL peptide alone, treated with 10 ng/mL TGF-β, or treated with peptide and TGF-β and incubated for 24 hours. At the end of the incubation time, the cells were imaged in the same location as in the original image to visualize closure of the scratch. The denuded area was calculated using ImageJ software and the percent wound closure was calculated for each treatment group.

Figure 5A:
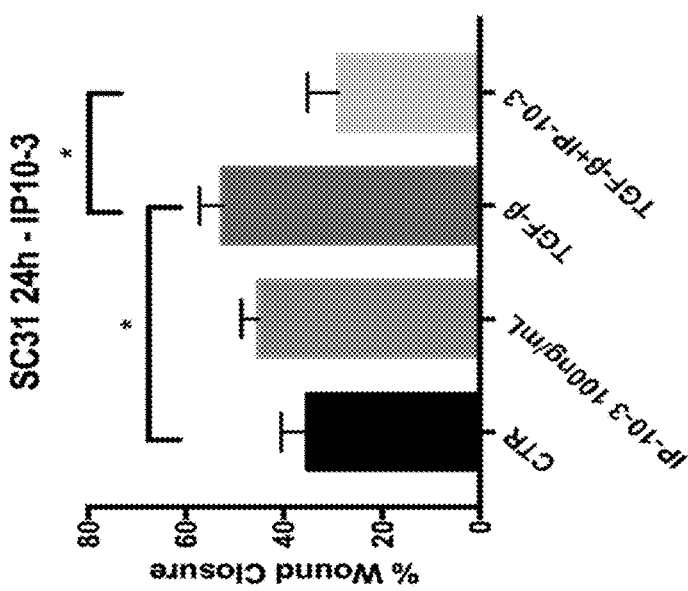
FIGS. 5A-5C: IP-10-3 peptide significantly reduces TGF-β-mediated induction in fibroblast migration. Following scratch assay, primary dermal fibroblasts treated with TGF-β (10 ng/mL) showed a significantly increased rate of wound closure.
Figure 5B:
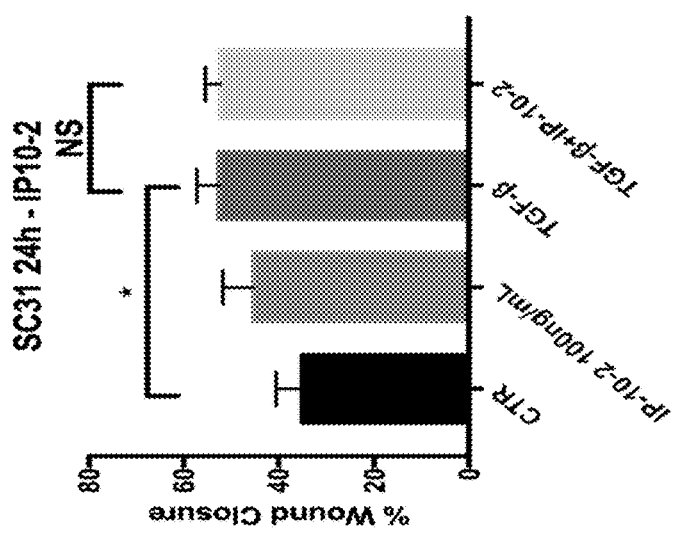
Figure 5C:
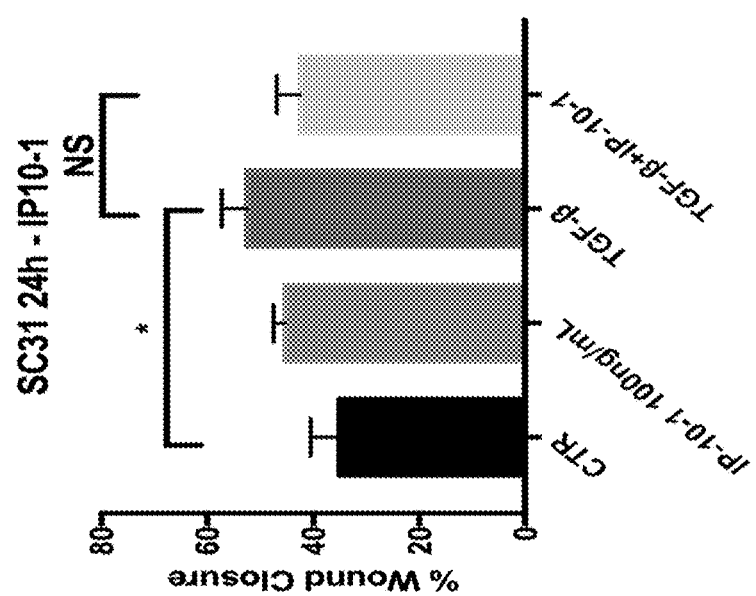

As shown in FIGS. 5A-5C, treatment with TGF-β significantly increased fibroblast migration, as measured by the amount of wound closure that had occurred by 24 hours. Treatment with 100 ng/mL IP-10-1 (SEQ ID NO: 2; FIG. 5A) or IP-10-2 (SEQ ID NO: 3; FIG. 5B) peptide did not affect the TGF-β-mediated induction in cell migration. However, in the presence of 100 ng/mL IP-10-3 peptide (SEQ ID NO: 4; FIG. 5C), the amount of TGF-β induced closure was significantly decreased back to the level of untreated cells. The peptides had no effect on fibroblast migration rate when applied to cells in the absence of TGF-β.

In view of the many possible embodiments to which the principles of the disclosure may be applied, it should be recognized that the illustrated embodiments are only preferred examples of the disclosure and should not be taken as limiting the scope of the disclosure. Rather, the scope of the disclosure is defined by the following claims.

The invention claimed is:

1. A synthetic peptide 12 to 30 amino acids in length, wherein the synthetic peptide comprises at least 12 consecutive amino acids of any one of SEQ ID NOs: 5-24 and 28-29.

2. The synthetic peptide of claim 1, comprising the amino acid sequence of any one of SEQ ID NOs: 5-24 and 28-29.

3. A synthetic peptide 12 to 30 amino acids in length, wherein the synthetic peptide comprises at least 12 consecutive amino acids of any one of SEQ ID NOs: 7, 9, 14, 17, 19 and 35-42.

4. A synthetic peptide comprising the amino acid sequence of any one of SEQ ID NOs: 5-42.

5. The synthetic peptide of claim 4, consisting of the amino acid sequence of any one of SEQ ID NOs: 5-42.

6. A composition comprising the synthetic peptide of claim 4 and a pharmaceutically acceptable carrier.

7. The composition of claim 6, wherein the composition further comprises at least one peptide selected from any one of SEQ ID NOs: 1-4.

8. A composition comprising two or more of the synthetic peptides of claim 4.

9. An isolated nucleic acid molecule encoding the synthetic peptide of claim 4.

10. The isolated nucleic acid molecule of claim 9, operably linked to a promoter.

11. A vector comprising the nucleic acid molecule claim 9.

12. The vector of claim 11, wherein the vector is a viral vector.

13. A composition comprising the synthetic peptide of claim 1 and a pharmaceutically acceptable carrier.

14. The composition of claim 13, wherein the composition further comprises at least one peptide selected from any one of SEQ ID NOs: 1-4.

15. A composition comprising two or more of the synthetic peptides of claim 1.

16. A composition comprising the synthetic peptide of claim 3 and a pharmaceutically acceptable carrier.

17. The composition of claim 16, wherein the composition further comprises at least one peptide selected from any one of SEQ ID NOs: 1-4.

18. A composition comprising two or more of the synthetic peptides of claim 3.

* * * * *

UNITED STATES PATENT AND TRADEMARK OFFICE
CERTIFICATE OF CORRECTION

PATENT NO. : 11,338,017 B2
APPLICATION NO. : 16/370603
DATED : May 24, 2022
INVENTOR(S) : Yates-Binder et al.

It is certified that error appears in the above-identified patent and that said Letters Patent is hereby corrected as shown below:

In the Claims

Column 58, Line 47, Claim 11, "molecule claim" should read –molecule of claim–

Signed and Sealed this
Twenty-fourth Day of January, 2023

Katherine Kelly Vidal
*Director of the United States Patent and Trademark Office*

```
                              SEQUENCE LISTING

<160> NUMBER OF SEQ ID NOS: 42

<210> SEQ ID NO 1
<211> LENGTH: 22
<212> TYPE: PRT
<213> ORGANISM: Artificial Sequence
<220> FEATURE:
<223> OTHER INFORMATION: Synthetic peptide

<400> SEQUENCE: 1

Pro Glu Ser Lys Ala Ile Lys Asn Leu Leu Lys Ala Val Ser Lys Glu
1               5                   10                  15

Met Ser Lys Arg Ser Pro
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic peptide

<400> SEQUENCE: 2

Pro Glu Ser Lys Val Ile Lys Asn Leu Leu Lys Val Ala Ser Lys Glu
1               5                   10                  15

Arg Ser Lys Arg Ser Pro
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide

<400> SEQUENCE: 3

Pro Glu Ser Arg Val Ile Lys Asn Leu Leu Arg Val Val Ser Lys Glu
1               5                   10                  15

Lys Ser Arg Arg Ser Pro
            20

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Phe Ala Lys Ala Ile Lys Asn Phe Ala Lys Ala Val Ala Lys Phe Ala
1               5                   10                  15

<210> SEQ ID NO 5
<211> LENGTH: 16
<212> TYPE: PRT
```

```
<213> ORGANISM: Artificial Sequence
<220> FEATURE:
<223> OTHER INFORMATION: Synthetic peptide

<400> SEQUENCE: 5

Val Arg Ser Thr Ser Ile Ser Gly Gly Ser Ile Ser Thr Ser Arg Val
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Ile Ile Pro Ala Ser Gln Phe Gly Gly Phe Pro Gln Ser Ala Pro Ile
1               5                   10                  15

Ile

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Phe Ser Pro Arg Val Glu Ile Gly Gly Ile Glu Val Arg Pro Ser Phe
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Phe Pro Met Phe Lys Gly Gly Lys Phe Met Pro Phe
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide

<400> SEQUENCE: 9

Arg Leu Ser Leu Ser Ile Gly Gly Ile Ser Leu Ser Arg
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

Asp Asp His Lys Glu Ile Asn Ala Gly Gly Ala Asn Ile Glu Lys His
1               5                   10                  15

Asp
```

```
<210> SEQ ID NO 11
<211> LENGTH: 13
<212> TYPE: PRT
<213> ORGANISM: Artificial Sequence
<220> FEATURE:
<223> OTHER INFORMATION: Synthetic peptide

<400> SEQUENCE: 11

Asp Asp His Lys Glu Ile Gly Gly Ile Glu Lys His Asp
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Phe Ser Pro His Val Glu Ile Gly Gly Ile Glu Val His Pro Ser Phe
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Phe Thr Pro His Val Glu Ile Gly Gly Ile Glu Val His Pro Thr Phe
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide

<400> SEQUENCE: 14

Phe Thr His Val Glu Ile Gly Gly Ile Glu Val His Thr Phe
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Ser Ile Ser Thr Ser Arg Val Gly Gly Val Arg Ser Thr Ser Ile Ser
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Phe Pro Gln Ser Ala Pro Ile Gly Gly Ile Ile Pro Ala Ser Gln Phe
1               5                   10                  15

<210> SEQ ID NO 17
```

```
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ile Glu Val Arg Pro Ser Phe Gly Gly Phe Ser Pro Arg Val Glu Ile
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Synthetic peptide

<400> SEQUENCE: 18

Lys Phe Met Pro Phe Gly Gly Phe Pro Met Phe Lys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic peptide

<400> SEQUENCE: 19

Ile Ser Leu Ser Arg Gly Gly Arg Leu Ser Leu Ser Ile
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide

<400> SEQUENCE: 20

Ala Asn Ile Glu Lys His Asp Gly Gly Asp Asp His Lys Glu Ile Asn
1               5                   10                  15

Ala

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide

<400> SEQUENCE: 21

Ile Glu Val His Pro Ser Phe Gly Gly Phe Ser Pro His Val Glu Ile
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic peptide

<400> SEQUENCE: 22

Ile Glu Val His Pro Thr Phe Gly Gly Phe Thr Pro His Val Glu Ile
1               5                   10                  15
```

```
<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Ile Glu Val His Thr Phe Gly Gly Phe Thr His Val Glu Ile
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide

<400> SEQUENCE: 24

Glu Lys His Asp Ile Gly Gly Asp Asp His Lys Glu Ile
1               5                   10

<210> SEQ ID NO 25
<211> LENGTH: 19
<212> TYPE: PRT
<213> ORGANISM: Artificial Sequence
<220> FEATURE:
<223> OTHER INFORMATION: Synthetic peptide

<400> SEQUENCE: 25

Asp Arg Phe Asn Ser Phe Arg Gln Pro Gly Gly Gln Arg Phe Ser Asn
1               5                   10                  15

Phe Arg Asp

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Phe Val Trp Gln Val Ala Ala Arg Val Gly Gly Val Arg Ala Ala Val
1               5                   10                  15

Gln Trp Val Phe
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Asp Gly Val Gln Pro Phe Asn Tyr Gln Gly Gly Gln Tyr Asn Phe Pro
1               5                   10                  15

Gln Val Gly Asp
            20

<210> SEQ ID NO 28
<211> LENGTH: 25
<212> TYPE: PRT
<213> ORGANISM: Artificial Sequence
<220> FEATURE:
<223> OTHER INFORMATION: Synthetic peptide
```

```
<400> SEQUENCE: 28

Asn Asp Ala Leu Ala Gly Leu Arg Met Leu Ile Arg Gly Gly Arg Ile
1               5                   10                  15

Met Arg Leu Gly Ala Leu Ala Asp Asn
            20                  25

<210> SEQ ID NO 29
<211> LENGTH: 14
<212> TYPE: PRT
<213> ORGANISM: Artificial Sequence
<220> FEATURE:
<223> OTHER INFORMATION: Synthetic peptide

<400> SEQUENCE: 29

Leu Arg Met Leu Ile Arg Gly Gly Arg Ile Leu Met Arg Leu
1               5                   10

<210> SEQ ID NO 30
<211> LENGTH: 19
<212> TYPE: PRT
<213> ORGANISM: Artificial Sequence
<220> FEATURE:
<223> OTHER INFORMATION: Synthetic peptide

<400> SEQUENCE: 30

Asp Arg Phe Asn Ser Tyr Arg Gln Pro Gly Gly Gln Arg Tyr Ser Asn
1               5                   10                  15

Phe Arg Asp

<210> SEQ ID NO 31
<211> LENGTH: 19
<212> TYPE: PRT
<213> ORGANISM: Artificial Sequence
<220> FEATURE:
<223> OTHER INFORMATION: Synthetic peptide

<400> SEQUENCE: 31

Asp Arg Tyr Asn Ser Tyr Arg Gln Pro Gly Gly Gln Arg Tyr Ser Asn
1               5                   10                  15

Tyr Arg Asp

<210> SEQ ID NO 32
<211> LENGTH: 20
<212> TYPE: PRT
<213> ORGANISM: Artificial Sequence
<220> FEATURE:
<223> OTHER INFORMATION: Synthetic peptide

<400> SEQUENCE: 32

Phe Val Trp Gln Val Phe Ala Arg Val Gly Gly Val Arg Ala Phe Val
1               5                   10                  15

Gln Trp Val Phe
            20

<210> SEQ ID NO 33
<211> LENGTH: 16
<212> TYPE: PRT
<213> ORGANISM: Artificial Sequence
<220> FEATURE:
<223> OTHER INFORMATION: Synthetic peptide

<400> SEQUENCE: 33

Phe Val Trp Phe Ala Arg Tyr Gly Gly Tyr Arg Ala Phe Trp Val Phe
```

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Asp Gly Phe Gln Pro Phe Asn Tyr Gln Gly Gly Gln Tyr Asn Phe Pro
1               5                   10                  15

Gln Phe Gly Asp
            20

<210> SEQ ID NO 35
<211> LENGTH: 25
<212> TYPE: PRT
<213> ORGANISM: Artificial Sequence
<220> FEATURE:
<223> OTHER INFORMATION: Synthetic peptide

<400> SEQUENCE: 35

Asn Asp Ala Leu Phe Gly Leu Arg Met Leu Ile Arg Gly Gly Arg Ile
1               5                   10                  15

Met Arg Leu Gly Phe Leu Ala Asp Asn
            20                  25

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide

<400> SEQUENCE: 36

Asn Asp Trp Leu Phe Arg Met Leu Ile Arg Gly Gly Arg Ile Met Arg
1               5                   10                  15

Phe Leu Trp Asp Asn
            20

<210> SEQ ID NO 37
<211> LENGTH: 17
<212> TYPE: PRT
<213> ORGANISM: Artificial Sequence
<220> FEATURE:
<223> OTHER INFORMATION: Synthetic peptide

<400> SEQUENCE: 37

Trp Leu Phe Arg Met Trp Ile Arg Gly Gly Arg Trp Met Arg Phe Leu
1               5                   10                  15

Trp

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

Leu Arg Phe Leu Ile Arg Gly Gly Arg Ile Leu Phe Arg Leu
1               5                   10

```
<210> SEQ ID NO 39
<211> LENGTH: 14
<212> TYPE: PRT
<213> ORGANISM: Artificial Sequence
<220> FEATURE:
<223> OTHER INFORMATION: Synthetic peptide

<400> SEQUENCE: 39

Leu Arg Phe Leu Phe Arg Gly Gly Arg Phe Leu Phe Arg Leu
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic peptide

<400> SEQUENCE: 40

Phe Arg Phe Leu Phe Arg Gly Gly Arg Phe Leu Phe Arg Phe
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Phe Arg Trp Leu Phe Arg Gly Gly Arg Phe Leu Trp Arg Phe
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic peptide

<400> SEQUENCE: 42

Phe Arg Trp Leu Trp Arg Gly Gly Arg Trp Leu Trp Arg Phe
1               5                   10
```